(12) United States Patent
Kim

(10) Patent No.: US 11,523,786 B2
(45) Date of Patent: *Dec. 13, 2022

(54) X-RAY INPUT APPARATUS, X-RAY IMAGING APPARATUS HAVING THE SAME, AND METHOD OF CONTROLLING THE X-RAY INPUT APPARATUS

(71) Applicant: Samsung Electronics Co., Ltd., Suwon-si (KR)

(72) Inventor: Myeong Je Kim, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

This patent is subject to a terminal disclaimer.

(21) Appl. No.: 17/247,959

(22) Filed: Dec. 31, 2020

(65) Prior Publication Data

US 2021/0153829 A1    May 27, 2021

Related U.S. Application Data

(63) Continuation of application No. 16/751,952, filed on Jan. 24, 2020, now Pat. No. 10,952,690, which is a
(Continued)

(30) Foreign Application Priority Data

May 18, 2017 (KR) .................. 10-2017-0061796
May 26, 2017 (KR) .................. 10-2017-0065465
Dec. 5, 2017 (KR) .................. 10-2017-0166236

(51) Int. Cl.
*A61B 6/00* (2006.01)

(52) U.S. Cl.
CPC .............. *A61B 6/467* (2013.01); *A61B 6/548* (2013.01); *A61B 6/4405* (2013.01);
(Continued)

(58) Field of Classification Search
CPC ........ A61B 6/467; A61B 6/548; A61B 6/4405; A61B 6/4411; A61B 6/4452; A61B 6/582; A61B 2560/0252
See application file for complete search history.

(56) References Cited

U.S. PATENT DOCUMENTS 9,750,477 B2   9/2017 Kitagawa et al.
9,851,708 B2  12/2017 Heijman et al.
(Continued)

FOREIGN PATENT DOCUMENTS

JP    2010191834 A    9/2010
JP    2012-070886 A   4/2012
(Continued)

OTHER PUBLICATIONS

Notice of Allowance dated Apr. 5, 2021 in connection with Korean Patent Application No. 10-2017-0166236, 3 pages.
(Continued)

*Primary Examiner* — Marcus H Taningco

(57) ABSTRACT

Disclosed herein are an X-ray input apparatus capable of exactly reflecting an operator's intention to perform calibration control, an X-ray imaging apparatus including the X-ray input apparatus, and a method of controlling the X-ray input apparatus. In accordance with an aspect of the present disclosure, an X-ray input apparatus comprises a body configured to be accommodated in a holder of an X-ray imaging apparatus. The apparatus also includes a touch sensor disposed on an outer circumferential surface of the body and configured to sense a touch. The apparatus also includes a radiation button disposed on a top of the body and configured to receive a control command from an operator. The apparatus also includes an input controller configured to
(Continued)

perform calibration control when the body is accommodated in the holder, thereby deciding a capacitance threshold value of the touch sensor.

21 Claims, 27 Drawing Sheets

Related U.S. Application Data continuation of application No. 15/982,788, filed on May 17, 2018, now Pat. No. 10,561,386.

(52) U.S. Cl.
CPC ........... *A61B 6/4411* (2013.01); *A61B 6/4452* (2013.01); *A61B 6/582* (2013.01); *A61B 2560/0252* (2013.01)

(56) References Cited

U.S. PATENT DOCUMENTS

| | | | |
|---|---|---|---|
| 10,952,690 B2* | 3/2021 | Kim | ........................ A61B 6/548 |
| 2006/0054833 A1 | 3/2006 | Tsuchino et al. | |
| 2010/0164479 A1* | 7/2010 | Alameh | ................ G06F 1/1626 324/115 |
| 2011/0073383 A1 | 3/2011 | Simmons | |
| 2017/0035383 A1 | 2/2017 | Liu et al. | |
| 2017/0196049 A1 | 7/2017 | Kim et al. | |
| 2017/0300166 A1 | 10/2017 | Rosenberg et al. | |
| 2018/0153499 A1 | 6/2018 | Tobita et al. | |

FOREIGN PATENT DOCUMENTS

| | | |
|---|---|---|
| JP | 5622908 B1 | 11/2014 |
| JP | 2015-535190 A | 12/2015 |
| JP | 5897020 B2 | 3/2016 |
| JP | 2017035137 A | 2/2017 |
| KR | 20040010099 A | 1/2004 |
| KR | 20150137802 A | 12/2015 |
| KR | 20200031157 A | 3/2020 |
| WO | 2017/022551 A1 | 2/2017 |

OTHER PUBLICATIONS

Supplementary European Search Report dated Mar. 9, 2020 in connection with European Patent Application No. 18 80 1918, 5 pages.

International Search Report dated Sep. 27, 2018 in connection with International Patent Application No. PCT/KR2018/005602, 3 pages.

Korean Intellectual Property Office "Detailed Ground(s) for Rejection " dated Nov. 2, 2021, in connection with KR 10-2021-0086975, 9 pages.

European Patent Office "Invitation pursuant to Rule 63(1) EPC" issued Aug. 10, 2021, in connection with European Patent Application No. 21170695.7, 3 pages.

European Patent Office, "Supplementary European Search Report" dated Nov. 29, 2021, in connection with European Patent Application No. 21170695.7, 6 pages.

* cited by examiner

X-RAY INPUT APPARATUS, X-RAY IMAGING APPARATUS HAVING THE SAME, AND METHOD OF CONTROLLING THE X-RAY INPUT APPARATUS

CROSS-REFERENCE TO RELATED APPLICATIONS

This application is a continuation of application Ser. No. 16/751,952, filed Jan. 24, 2020, which is a continuation of application Ser. No. 15/982,788, filed May 17, 2018, now U.S. Pat. No. 10,561,386, which claims priority to Korean Patent Application No. 10-2017-0061796, filed May 18, 2017, Korean Patent Application No. 10-2017-0065465, filed May 26, 2017, and Korean Patent Application No. 10-2017-0166236, filed Dec. 5, 2017, the disclosures of which are incorporated by reference herein in their entirety.

BACKGROUND

1. Field

The present disclosure relates to an X-ray imaging apparatus for acquiring an image of an object to diagnose various diseases, and more particularly, to an X-ray input apparatus for controlling an X-ray imaging apparatus, and a method of controlling the X-ray input apparatus.

2. Description of the Related Art

In medical treatment, clinical diagnosis has a large part in treating patients, and the development of medical technologies contributed greatly to accurate clinical diagnosis. Dependency of patient treatment on clinical diagnosis is predicted to increase more and more in future.

Accordingly, image diagnostic apparatuses, such as Computer Tomography (CT), Magnetic Resonance Imaging (MM), and an X-ray imaging apparatus, became essential equipment in modern medical treatment.

Recently, a wireless X-ray input apparatus has been introduced to conveniently control the image diagnostic apparatuses. However, the wireless X-ray input apparatus needs to recognize a user's inputs accurately when carried by the user.

SUMMARY

Therefore, it is an aspect of the present disclosure to provide an X-ray input apparatus capable of exactly reflecting an operator's intention to perform calibration control, an X-ray imaging apparatus including the X-ray input apparatus, and a method of controlling the X-ray input apparatus.

It is another aspect of the present disclosure to provide an X-ray input apparatus capable of performing calibration control, an X-ray imaging apparatus including the X-ray input apparatus, and a method of controlling the X-ray input apparatus.

Additional aspects of the disclosure will be set forth in part in the description which follows and, in part, will be obvious from the description, or may be learned by practice of the disclosure.

In accordance with an aspect of the present disclosure, an X-ray input apparatus comprises a body configured to be accommodated in a holder of an X-ray imaging apparatus; a touch sensor disposed on an outer circumferential surface of the body, the touch sensor configured to sense a touch; a radiation button disposed on a top of the body, and configured to receive a control command from an operator; and an input controller configured to perform calibration control while the body is accommodated in the holder, thereby deciding a capacitance threshold value of the touch sensor.

The X-ray input apparatus further may comprise a position sensor configured to sense a position of the X-ray input apparatus.

The input controller may perform the calibration control when an output of the position sensor represents that the X-ray input apparatus is accommodated in the holder.

The input controller may perform the calibration control when the body is accommodated in the holder, and the radiation button is pressed.

The radiation button may comprise a one-step button configured to receive an X-ray radiation preparation command, and a two-step button configured to receive an X-ray radiation command, the one-step button outputs a first signal when a predetermined pressure is applied on the one-step button, and wherein the two-step button outputs a second signal when predetermined pressure is applied on the two-step button.

When the body is accommodated in the holder, and the first signal is output from the radiation button, the input controller may perform the calibration control.

When the body is accommodated in the holder, the input controller may receive a capacitance value of the touch sensor, and may perform the calibration control based on the capacitance value of the touch sensor.

In accordance with another aspect of the present disclosure, an X-ray input apparatus comprises a body configured to be accommodated in a holder of an X-ray imaging apparatus; a touch sensor disposed on an outer circumferential surface of the body, the touch sensor configured to sense a touch; an environment sensor disposed at an area of the body, the environment sensor configured to sense surrounding environment information; a radiation button disposed on a top of the body, the radiation button configured to receive a control command from an operator; and an input controller configured to perform calibration control when an output of the environment sensor is out of a reference range, thereby deciding a capacitance threshold value of the touch sensor.

The environment sensor may comprise at least one of a temperature sensor or a humidity sensor.

The environment sensor may sense the surrounding environment information at predetermined time periods.

The input controller may reset the reference range when the calibration control is performed.

If an output of the environment sensor is different by a reference value or more from surrounding environment information sensed when the calibration control was previously performed, the input controller may determine that the output of the environment sensor is out of the reference range.

When the output of the environment sensor is out of the reference range, and the body is accommodated in the holder, the input controller may perform the calibration control.

When the output of the environment sensor is out of the reference range, and an output of the touch sensor exceeds the capacitance threshold value, the input controller may perform the calibration control.

In accordance with another aspect of the present disclosure, an X-ray input apparatus comprises a body configured to be accommodated in a holder of an X-ray imaging apparatus; a touch sensor disposed on an outer circumferential surface of the body, the touch sensor configured to sense a touch; a radiation button disposed on a top of the body, the radiation button configured to receive a control command from an operator; a calibration button disposed on one surface of the body, the calibration button configured to receive a control command from the operator; and an input controller configured to perform calibration control when the calibration button and the radiation button are pressed, thereby deciding a capacitance threshold value of the touch sensor.

The radiation button may comprise a one-step button configured to receive an X-ray radiation preparation command, and a two-step button configured to receive an X-ray radiation command, the one-step button outputs a first signal when predetermined pressure is applied on the one-step button, and wherein the two-step button outputs a second signal when predetermined pressure is applied on the two-step button.

The calibration button may output a third signal when pressure is applied on the calibration button, and the wherein input controller may perform the calibration control in response to the first signal being output from the radiation button and the third signal being output from the calibration button.

The input controller is further configured to perform the calibration control when the calibration button and the radiation button are pressed and an output of the touch sensor exceeds the capacitance threshold value.

In accordance with another aspect of the present disclosure, an X-ray imaging apparatus comprise an X-ray input apparatus comprising a body, a holder configured to accommodate the X-ray apparatus, a touch sensor disposed on an outer circumferential surface of the body, the touch configured to sense a touch, a radiation button disposed on a top of the body, the radiation button configured to receive a control command from an operator, an input controller configured to perform calibration control while the body is accommodated in the holder, thereby deciding a capacitance threshold value of the touch sensor, an X-ray source configured to generate X-rays and to irradiate the X-rays, a high-voltage generator configured to apply a high voltage to the X-ray source, and a main controller configured to transmit at least one of an X-ray radiation preparation signal or an X-ray radiation signal to the high-voltage generator according to a control command input to the radiation button.

The X-ray imaging apparatus may further comprise a position sensor configured to sense a position of the X-ray input apparatus.

The input controller may perform the calibration control when an output of the position sensor represents that the X-ray input apparatus is accommodated in the holder.

When the body is accommodated in the holder, and the radiation button is pressed, the input controller may perform the calibration control.

The X-ray input apparatus may further comprise an input communication device configured to communicate with the holder, and the holder may further comprise a holder communication device configured to communicate with the X-ray input apparatus; and a holder controller configured to transmit, when the holder communication device receives the operator's control command from the X-ray input apparatus, the operator's control command to the main controller.

In accordance with another aspect of the present disclosure, a method of controlling an X-ray input apparatus, the X-ray input apparatus including a body configured to be accommodated in a holder, a radiation button disposed on a top of the body, and configured to receive a control command from an operator, and a touch sensor disposed on an outer circumferential surface of the body, the method comprises sensing a position of the body; determining whether the body is accommodated in the holder, based on the sensed position of the body; and performing calibration control when the body is accommodated in the holder, thereby deciding a capacitance threshold value of the touch sensor.

The performing of the calibration control may comprise performing the calibration control when the body is accommodated in the holder and the radiation button is pressed.

The performing of the calibration control may comprise receiving a capacitance value of the touch sensor when the body is accommodated in the holder, and performing the calibration control based on the received capacitance value of the touch sensor.

In accordance with another aspect of the present disclosure, computer-readable recording medium storing a program for executing an X-ray radiation control method, the X-ray radiation control method comprises controlling a touch screen of a mobile device to display an X-ray radiation preparation button for receiving an X-ray radiation preparation command, and an X-ray radiation button for receiving an X-ray radiation command; transmitting an X-ray radiation preparation signal to an X-ray imaging apparatus, when a touch made on an area corresponding to the X-ray radiation preparation button is sensed; transmitting an X-ray radiation signal to the X-ray imaging apparatus, when a touch made on an area corresponding to the X-ray radiation button is sensed; and transmitting neither the X-ray radiation preparation signal nor the X-ray radiation signal, when a touch made on the remaining area except for the areas corresponding to the X-ray radiation preparation button and the X-ray radiation button is sensed.

Before undertaking the DETAILED DESCRIPTION below, it may be advantageous to set forth definitions of certain words and phrases used throughout this patent document: the terms "include" and "comprise," as well as derivatives thereof, mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and the term "controller" means any device, system or part thereof that controls at least one operation, such a device may be implemented in hardware, firmware or software, or some combination of at least two of the same. It should be noted that the functionality associated with any particular controller may be centralized or distributed, whether locally or remotely.

Moreover, various functions described below can be implemented or supported by one or more computer programs, each of which is formed from computer readable program code and embodied in a computer readable medium. The terms "application" and "program" refer to one or more computer programs, software components, sets of instructions, procedures, functions, objects, classes, instances, related data, or a portion thereof adapted for implementation in a suitable computer readable program code. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive, a compact disc (CD), a digital video disc (DVD), or any other type of memory. A "non-transitory" computer readable medium excludes wired, wireless, optical, or other communication links that transport transitory electrical or other signals. A non-transitory computer readable medium includes media where data can be permanently stored and media where data can be stored and later overwritten, such as a rewritable optical disc or an erasable memory device.

Definitions for certain words and phrases are provided throughout this patent document, those of ordinary skill in the art should understand that in many, if not most instances, such definitions apply to prior, as well as future uses of such defined words and phrases.

BRIEF DESCRIPTION OF THE DRAWINGS

These and/or other aspects of the disclosure will become apparent and more readily appreciated from the following description of the embodiments, taken in conjunction with the accompanying drawings of which.

DETAILED DESCRIPTION

FIGS. 1 through 27, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably arranged system or device.

Hereinafter, an X-ray input apparatus and a control method thereof according to the present disclosure will be described in detail with reference to the accompanying drawings.

The X-ray input apparatus according to the present disclosure may be carried by an operator, and the operator can control an X-ray imaging apparatus using the X-ray input apparatus in a wireless fashion.

Hereinafter, for convenience of description, a configuration of an X-ray imaging apparatus that underlies the present disclosure will be briefly described, and then the X-ray input apparatus according to the present disclosure will be described.

Figure 1:
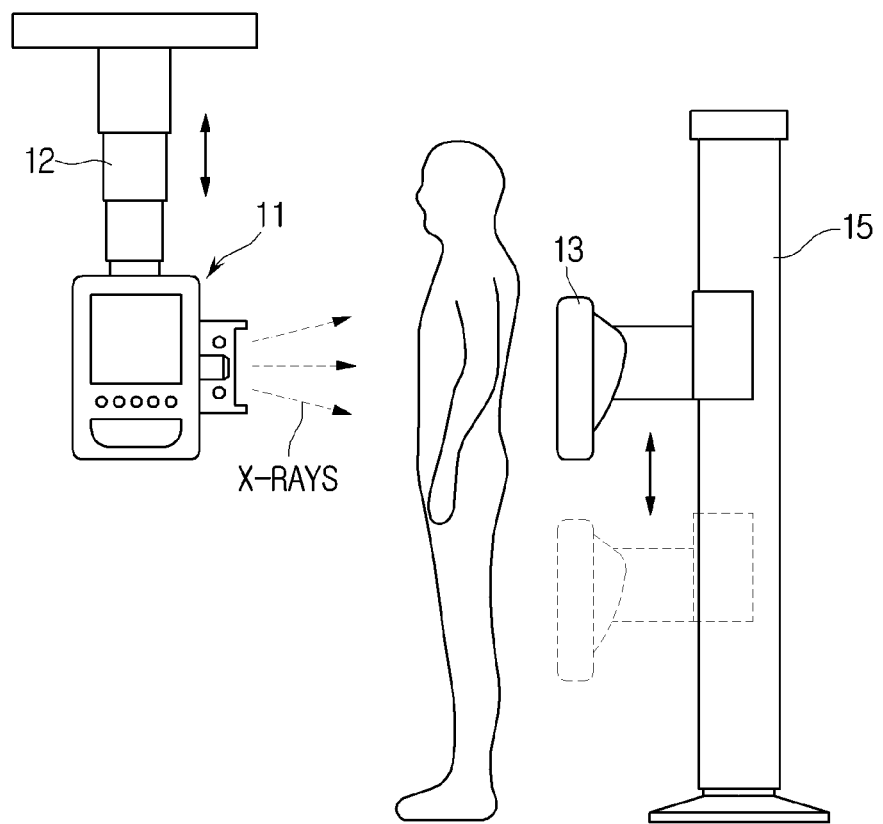
FIG. 1 illustrates an outer appearance of a general X-ray imaging apparatus 10.
Figure 2:
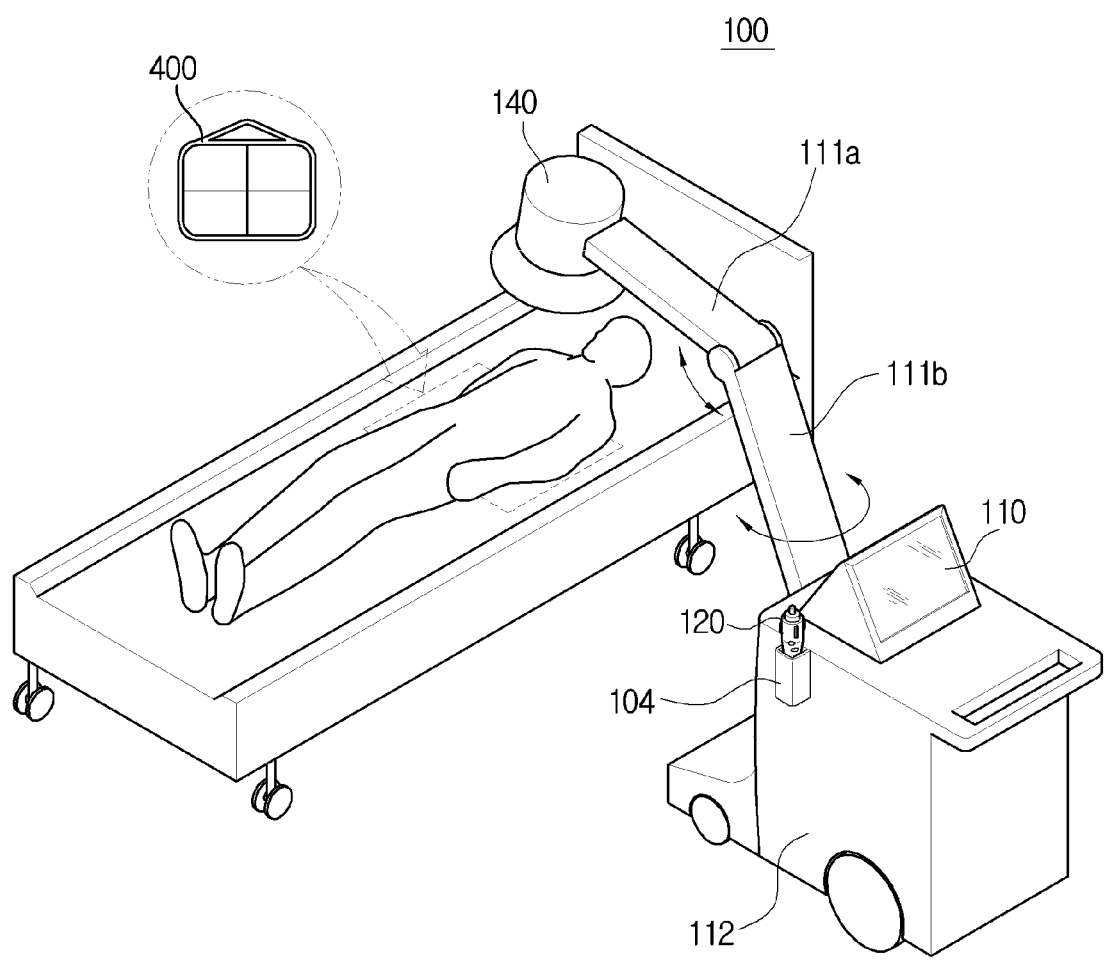
FIG. 2 illustrates an outer appearance of a mobile X-ray imaging apparatus.

FIG. 1 illustrates an outer appearance of a general X-ray imaging apparatus 10, and FIG. 2 illustrates an outer appearance of a mobile X-ray imaging apparatus 100.

As shown in FIG. 1, in the general X-ray imaging apparatus 10, an X-ray source 11 and an X-ray detector 13 may be fixed in predetermined space. The X-ray source 11 may be connected to an arm 12 installed on the ceiling of an examination room, and the X-ray detector 13 may be connected to a housing 15 fixed on the floor of the examination room.

The arm 12 connected to the X-ray source 11 can extend vertically to move the X-ray source 11 vertically with respect to the floor. The X-ray detector 13 may also be movable vertically along the housing 15. That is, in the general X-ray imaging apparatus 10, the X-ray source 11 and the X-ray detector 13 may be movable only in a predetermined direction in the predetermined space.

Referring to FIG. 2, in the mobile X-ray imaging apparatus 100, an X-ray source 140 and an X-ray detector 400 may be movable freely in arbitrary 3Dimensional (3D) space. More specifically, the X-ray source 140 may be installed in a movable main body 112 through a support arm 111$a$, and the support arm 111$a$ may be connected to a support frame 111$b$ in such a way to be rotatable in an up-down direction. The support frame 111$b$ may be connected to one side of the main body 112 in such a way to be rotatable horizontally. As a result, the support arm 111$a$ may be rotatable, and accordingly, an angle of the support arm 111$a$ may change so that the X-ray source 140 can move freely. Also, the X-ray detector 400 of the mobile X-ray imaging apparatus 100 may be a portable X-ray detector, and accordingly, the X-ray detector 400 may also be positioned at an arbitrary location in the 3D space.

In one side of the main body 112, a holder 104 may be disposed to accommodate an X-ray input apparatus 120 therein. When an operator does not use the X-ray input apparatus 120, the operator can put the X-ray input apparatus 120 in the holder 104 to keep the X-ray input apparatus 120. When the operator uses the X-ray input apparatus 120, the operator can take the X-ray input apparatus 120 out of the holder 104 to use the X-ray input apparatus 120.

Hereinafter, a structure of the X-ray input apparatus 120 will be described, and then operations of the X-ray input apparatus 120 and the X-ray imaging apparatus 100 will be described in detail.

Figure 3:
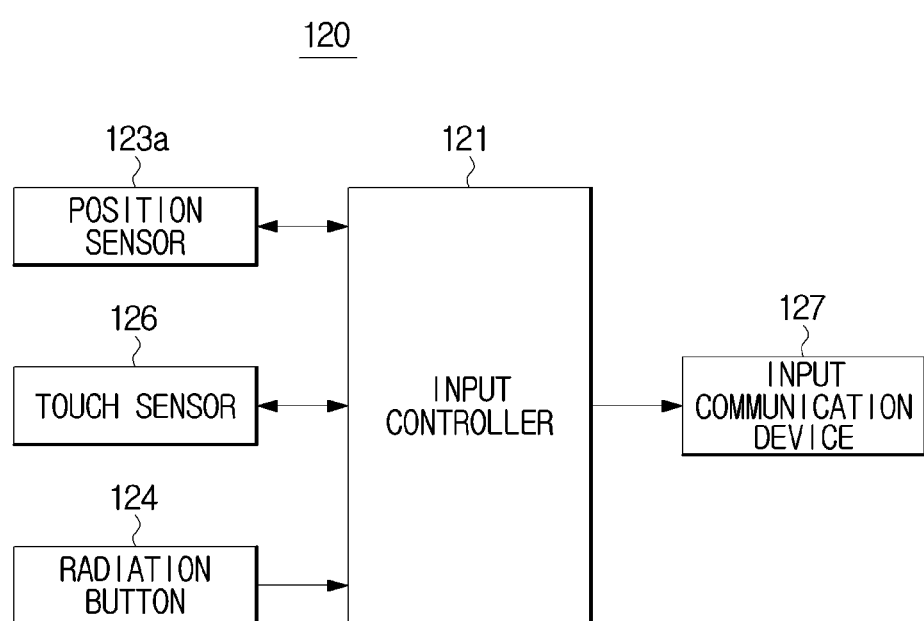
FIG. 3 illustrates a control block diagram of an X-ray input apparatus according to an embodiment.
Figure 4:
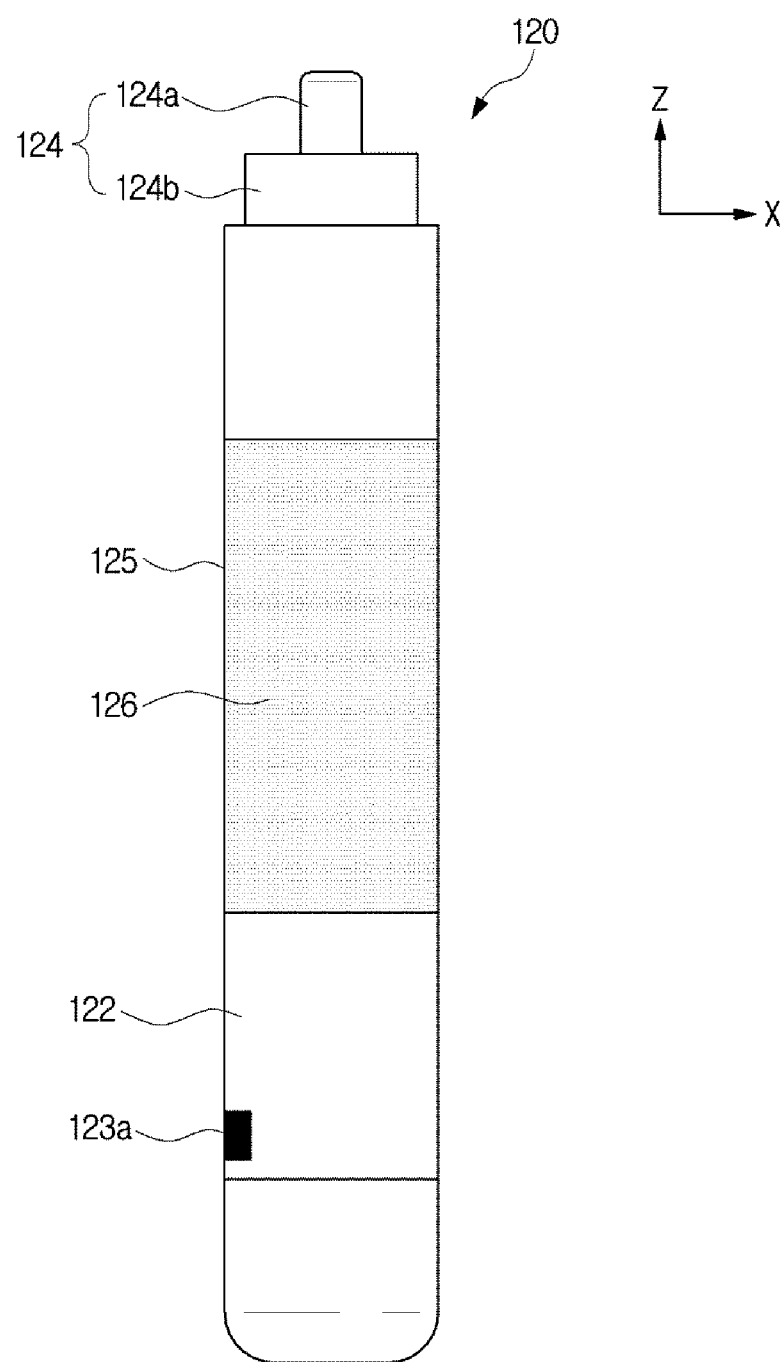
FIG. 4 illustrates a structure of an X-ray input apparatus according to an embodiment.
Figure 5:
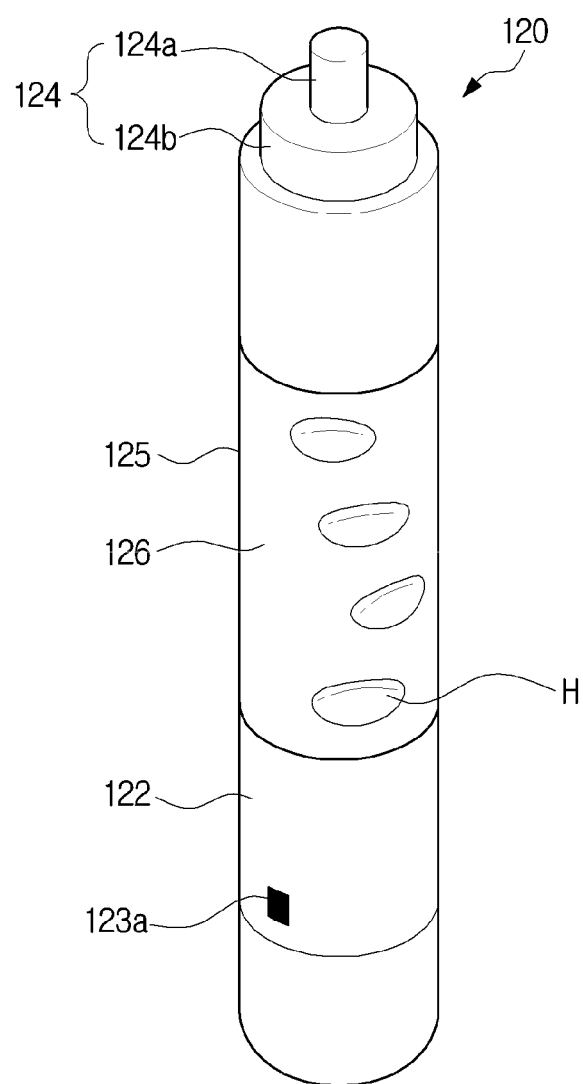
FIG. 5 illustrates an example of a grip area of an X-ray input apparatus.
Figure 6:
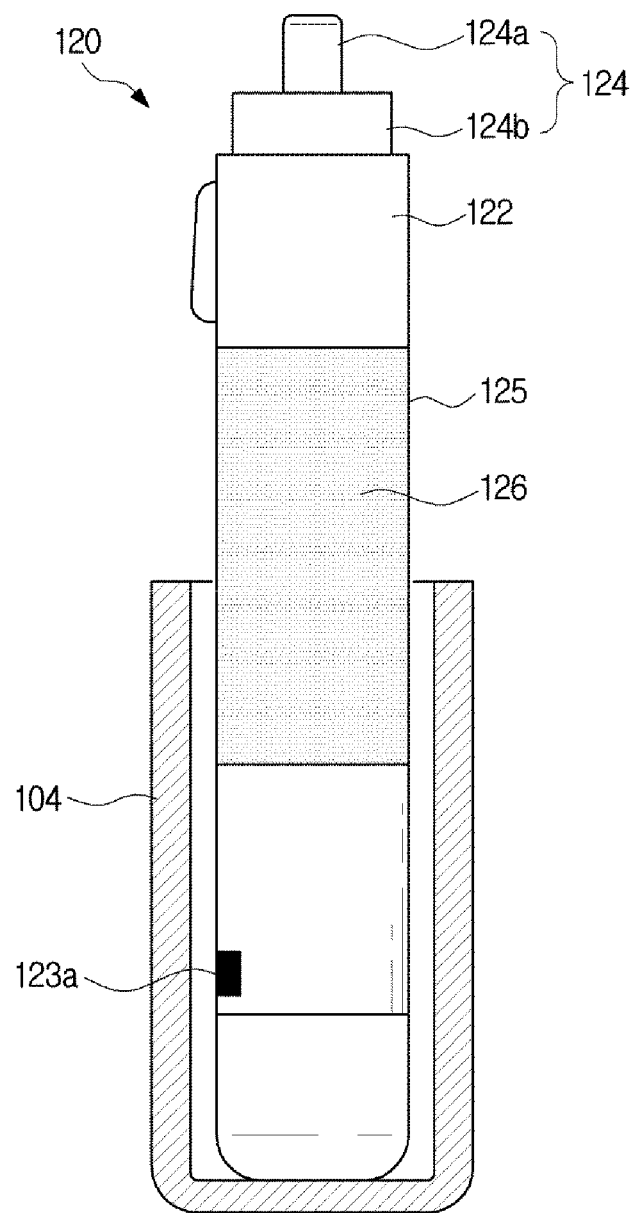
FIG. 6 illustrates the X-ray input apparatus of FIG. 4 when the X-ray input apparatus is accommodated in a holder.

FIG. 3 illustrates a control block diagram of an X-ray input apparatus according to an embodiment, FIG. 4 illustrates a structure of an X-ray input apparatus according to an embodiment, FIG. 5 illustrates an example of a grip area of an X-ray input apparatus, and FIG. 6 illustrates the X-ray input apparatus of FIG. 4 when the X-ray input apparatus is accommodated in a holder.

Referring to FIG. 3, the X-ray input apparatus 120 may include a position sensor 123a for detecting a position of the X-ray input apparatus 120, a touch sensor 126 for sensing a touch, a radiation button 124 for receiving an X-ray radiation command, an input controller 121 for controlling operations of the X-ray input apparatus 120, and an input communication device 127 for transmitting/receiving signals through communication with the holder 104.

Referring to FIGS. 3, 4, and 5, the X-ray input apparatus 120 may include a body 122 that can be accommodated in the holder 104, and a grip area 125 formed on an outer circumferential surface of the body 122, wherein the radiation button 124 may be disposed on a top of the body 122.

The grip area 125 may be gripped by a user who uses the X-ray input apparatus 120, particularly, who operates the radiation button 124 while carrying the X-ray input apparatus 120. For example, the grip area 125 may be positioned at a center area in z-axis direction of the body 122, or the grip area 125 may be positioned adjacent to the radiation button 124.

The touch sensor 126 may be driven in a capacitive method.

The touch sensor 126 may be disposed along an outer circumferential surface of the grip area 125. The touch sensor 126 may be in the form of a touch sensor surrounding the outer circumferential surface of the body 122, or may be in the form of a plurality of touch sensors arranged at regular intervals.

The touch sensor 126 may be positioned at any location as long as the operator's hand can contact the touch sensor 126 when the operator grips the X-ray input apparatus 120.

If the touch sensor 126 is positioned on the grip area 125, as described above, the touch sensor 126 may sense the operator's touch when the operator grips the body 122. If the touch sensor 126 senses the operator's touch, the X-ray input apparatus 120 may determine that the operator has gripped the X-ray input apparatus 120.

Also, in the grip area 125, an engraved pattern H formed in the shape of fingers may be formed for the operator to be able to easily grip the X-ray input apparatus 120, as shown in FIG. 5. Also, the engraved pattern H may guide the operator to grip the X-ray input apparatus 120 at an appropriate position.

The touch sensor 126 may be formed in the remaining area of the grip area 125 except for the engraved pattern H, or may be formed in a predetermined area of the grip area 125 including the engraved pattern H. When the touch sensor 126 is formed in the remaining area of the grip area 125 except for the engraved pattern H, the touch sensor 126 may be formed in the rear surface of the grip area 125 that is opposite to the engraved pattern H.

If the touch sensor 126 is formed in the rear surface of the grip area 125 that is opposite to the engraved pattern H, the touch sensor 126 can collect touch input information immediately when the operator grips the X-ray input apparatus 120, and accordingly, it is possible to improve the input accuracy of an X-ray radiation command and a calibration control command.

However, the touch sensor 126 may be not necessarily disposed in the rear surface of the grip area 125 that is opposite to the engraved pattern H. That is, the touch sensor 126 may be positioned at any area which the operator's hand contacts when the operator grips the X-ray input apparatus 120 on the engraved pattern H, and the location relationship between the engraved pattern H and the touch sensor 126 is not limited thereto.

Referring to FIG. 6, the position sensor 123a may be disposed at one area of the body 122 to collect information about whether the X-ray input apparatus 120 is accommodated in the holder 104.

For example, the position sensor 123a may be disposed at a lower area of the body 122 of the X-ray input apparatus 120. However, the location of the position sensor 123a is not limited to this, and the position sensor 123a may be positioned at any location where the position sensor 123a can sense whether the X-ray input apparatus 120 is accommodated in the holder 104.

The position sensor 123a may include at least one of a magnetic field sensor, a limit switch, an optical sensor, and an ultrasonic sensor. For example, if the position sensor 123a includes a magnetic field sensor, a magnet may be disposed at an area of the holder 104 corresponding to the position sensor 123a.

Also, if the position sensor 123a includes an optical sensor or an ultrasonic sensor, the position sensor 123a may include a sender for sending light (for example, infrared light or visible light) or ultrasonic waves, and a receiver for receiving light or ultrasonic waves reflected from an inner wall of the holder 104. Also, the X-ray input apparatus 120 may include the receiver, and the sender may be installed in the holder 104. However, the kind of the position sensor 123a is not limited to the above-described examples.

A reference value representing that the body 122 is accommodated in the holder 104 may have been stored in advance according to the kind of the position sensor 123a. The reference value may have been stored as a predetermined reference range.

The input controller 121 may compare an output of the position sensor 123a to the reference value to determine whether the body 122 is accommodated in the holder 104.

Figure 7:
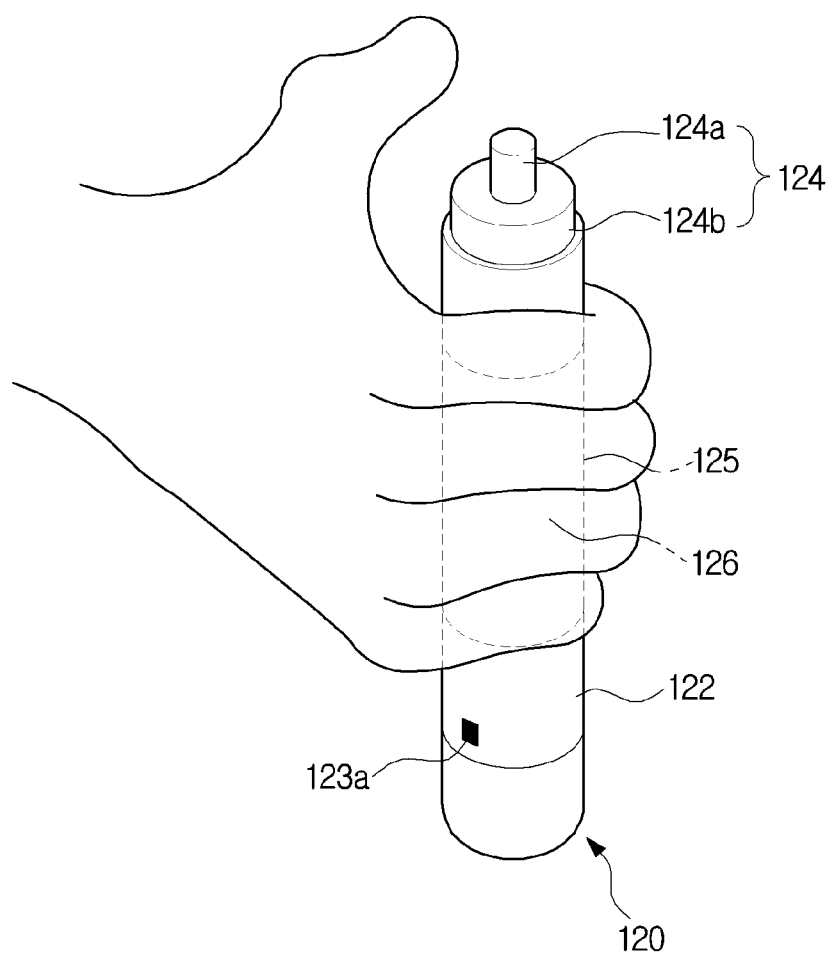
FIGS. 7 to 9 illustrate views for describing an operation in which an X-ray input apparatus receives a control command from an operator.
Figure 8:
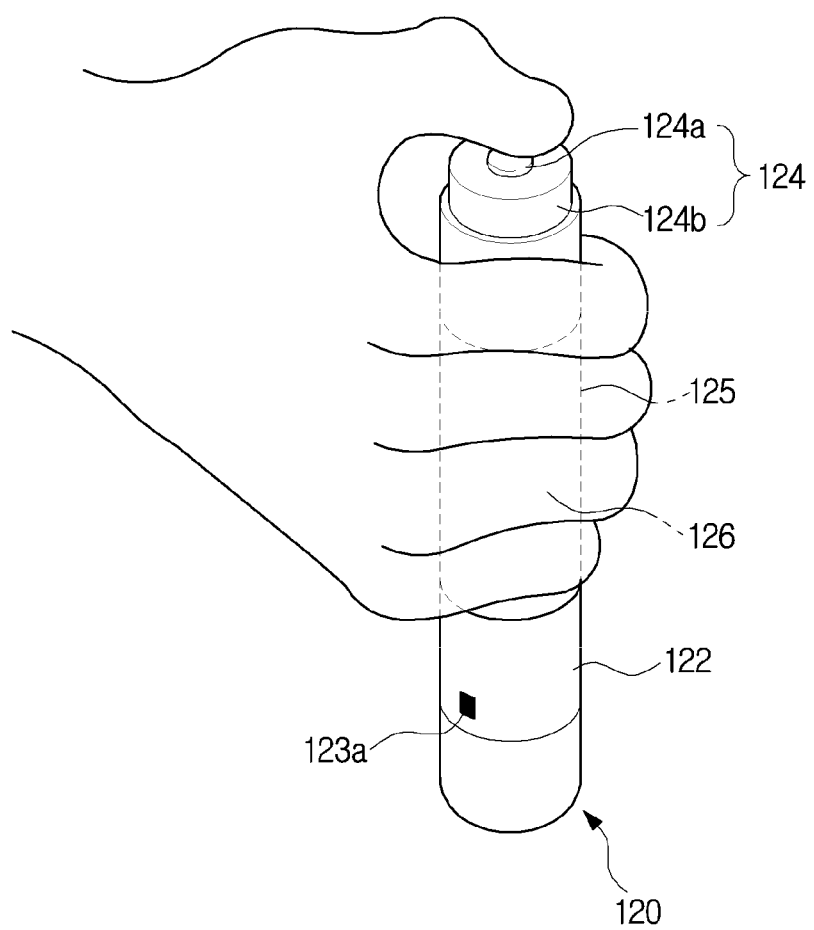
Figure 9:
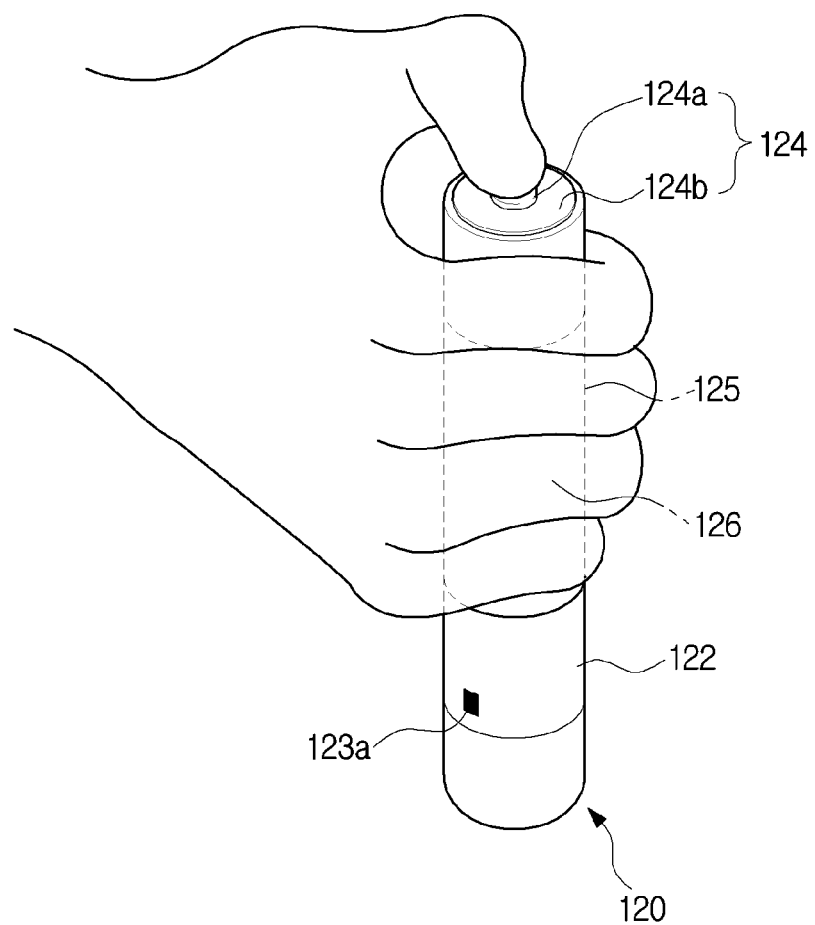

FIGS. 7 to 9 illustrates views for describing an operation in which an X-ray input apparatus receives a control command from an operator.

Referring to FIG. 7, the radiation button 124 may be disposed on the top of the body 122. The radiation button 124 may be in the form of a two-step switch protruding from the top of the body 122. The radiation button 124 may include a one-step button 124a for receiving a ready command, and a two-step button 124b for receiving a radiation command.

A ready command and a radiation command input through the radiation button 124 may be used in a process for deciding a control command for the X-ray input apparatus 120 or the X-ray imaging apparatus 100, together with touch information input to the touch sensor 126 or location information collected from the position sensor 123a.

The operator may grip the X-ray input apparatus 120 on the grip area 125. For example, the operator may grip the grip area 125 with the operator's four fingers except for the operator's thumb. When the operator grips the grip area 125, the operator's hand may contact the touch sensor 126 disposed on the grip area 125, and accordingly, the touch sensor 126 may sense the operator's touch. In this state, the operator may press the radiation button 124 protruding from the top of the body 122 to input a control command.

If the operator presses the radiation button 124 to set a ready state when the operator's touch is sensed by the touch sensor 126, as shown in FIG. 8, a ready command instructing preheating for irradiating X-rays may be input. For example, the operator may apply pressure being in a range of first threshold pressure to second threshold pressure on the one-step button 124a for receiving a ready command, to input a first command. The first command may be an X-ray radiation preparation command. In this example, the entire or a part of the one-step button 124a may be inserted into the inside of the two-step button 124b.

Then, as shown in FIG. 9, if the operator further applies pressure on the radiation button 124 to set a radiation state when the operator's touch is sensed by the touch sensor 126 and the radiation button 124 is pressed to set the ready state, a radiation command for actually radiating X-rays may be input. For example, the operator may apply pressure that is higher than or equal to the second threshold pressure, on the radiation button 124 to thus input a second command, wherein the second command may be an X-ray radiation command. In this example, the entire or a part of the two-step button 124b may be inserted into the inside of the body 122.

The first threshold pressure may be equal to or lower than the second threshold pressure. That is, after the one-step button 124a is inserted into the inside of the two-step button 124b to input the X-ray radiation preparation command, the same pressure may continue to be applied to input an X-ray radiation command, or higher pressure may be applied than that applied when the X-ray radiation preparation command is input, to input an X-ray radiation command.

In various embodiments, an X-ray radiation command may be input after an X-ray radiation preparation command is input. That is, X-rays may be irradiated after an X-ray radiation preparation command is input.

Hereinafter, calibration control of the touch sensor 126 will be described.

Figure 10:
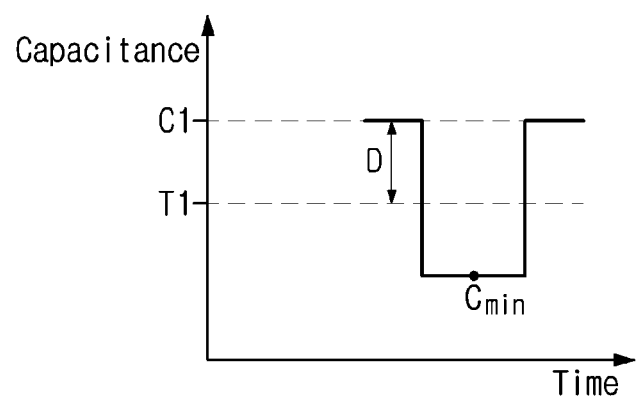
FIG. 10 illustrates a graph showing a capacitance threshold value that is set by calibration control of an X-ray imaging apparatus according to an embodiment.

FIG. 10 illustrates a graph showing a capacitance threshold value that is set by calibration control of an X-ray imaging apparatus according to an embodiment.

Calibration control of the touch sensor 126 may be performed to decide a capacitance threshold value of the touch sensor 126 based on a capacitance threshold reference value of the touch sensor 126. The capacitance reference value may be a capacitance value measured when no external contact is made on the touch sensor 126, and the capacitance threshold value may be a capacitance value based on which a change in capacitance caused by external stimulus is recognized as an operator's touch stimulus. That is, when no external contact is made on the touch sensor 126, a capacitance value exceeding the capacitance threshold value may be measured, and when an external contact is made on the touch sensor 126, a capacitance value that is equal to or smaller than the capacitance threshold value may be measured.

Since the capacitance reference value of the touch sensor 126 depends on a surrounding environment such as temperature and humidity, touch sensitivity of the touch sensor 126 may also depend on the surrounding environment. Accordingly, the capacitance threshold value of the touch sensor 126 may be changed through calibration control of the touch sensor 126. A process of resetting a capacitance threshold value based on a changed capacitance reference value of the touch sensor 126 is called calibration control of the touch sensor 126.

As seen in the graph of FIG. 10, the input controller 121 may receive an output value of the touch sensor 126, and use the output value of the touch sensor 126 as a capacitance reference vale C1. The output value of the touch sensor 126 to be used as the capacitance reference value C1 may be a value measured when calibration control is performed, or a value measured when a calibration control command is input. Or, the output value of the touch sensor 126 to be used as the capacitance reference value C1 may be a value measured at any time between when a calibration control command is input and when calibration control is performed.

A minimum value D of changes in capacitance that may be caused by a contact may have been stored in advance, and the input controller 121 may decide a capacitance threshold value T1 based on the capacitance reference value C1 and the minimum value D of changes in capacitance. For example, the input controller 121 may decide a value obtained by subtracting the minimum value D of changes in capacitance from the capacitance reference value C1, as the capacitance threshold value T1.

If calibration is performed normally according to the above-described operations, the capacitance threshold value T1 may be decided as a value between the capacitance reference value C1 and a capacitance minimum value $C_{min}$ that is caused by the operator's touch.

Hereinafter, a method in which an operator inputs a calibration control command will be described.

Referring again to FIG. 6, the X-ray input apparatus 120 according to an embodiment may perform calibration control when the X-ray input apparatus 120 is accommodated in the holder 104. Accordingly, the input controller 121 may perform calibration control when an output from the position sensor 123a represents that the X-ray input apparatus 120 is accommodated in the holder 104.

As described above, the input controller 121 may have already stored a reference value representing that the X-ray input apparatus 120 is accommodated in the holder 104. If an output of the position sensor 123a is identical to the reference value, the input controller 121 may determine that the X-ray input apparatus 120 is accommodated in the holder 104.

Meanwhile, if calibration control is performed when a touch is made on the touch sensor 126, a smaller capacitance reference value C1 may be measured than when no contact is made on the touch sensor 126, and as a result, a calibration error may occur so that a smaller capacitance threshold value T1 is decided than when no contact is made on the touch sensor 126. In one or more embodiments, the capacitance threshold value T1 may be smaller than the capacitance minimum value $C_{min}$.

However, the capacitance threshold value being set to an abnormally small value due to a calibration error can be prevented if calibration control is performed only while the X-ray input apparatus 120 is accommodated in the holder 104, like the above-described embodiment. Accordingly, the input accuracy of a calibration control command can be improved compared to when calibration control is performed regardless of whether the X-ray input apparatus 120 is accommodated in the holder 104.

Furthermore, by additionally using an output of the touch sensor 126 to determine whether to perform calibration control, the accuracy of calibration control can also be improved. In this example, the input controller 121 may perform calibration control, when the X-ray input apparatus 120 is accommodated in the holder 104 and an output of the touch sensor 126 exceeds the capacitance threshold value.

Figure 11:
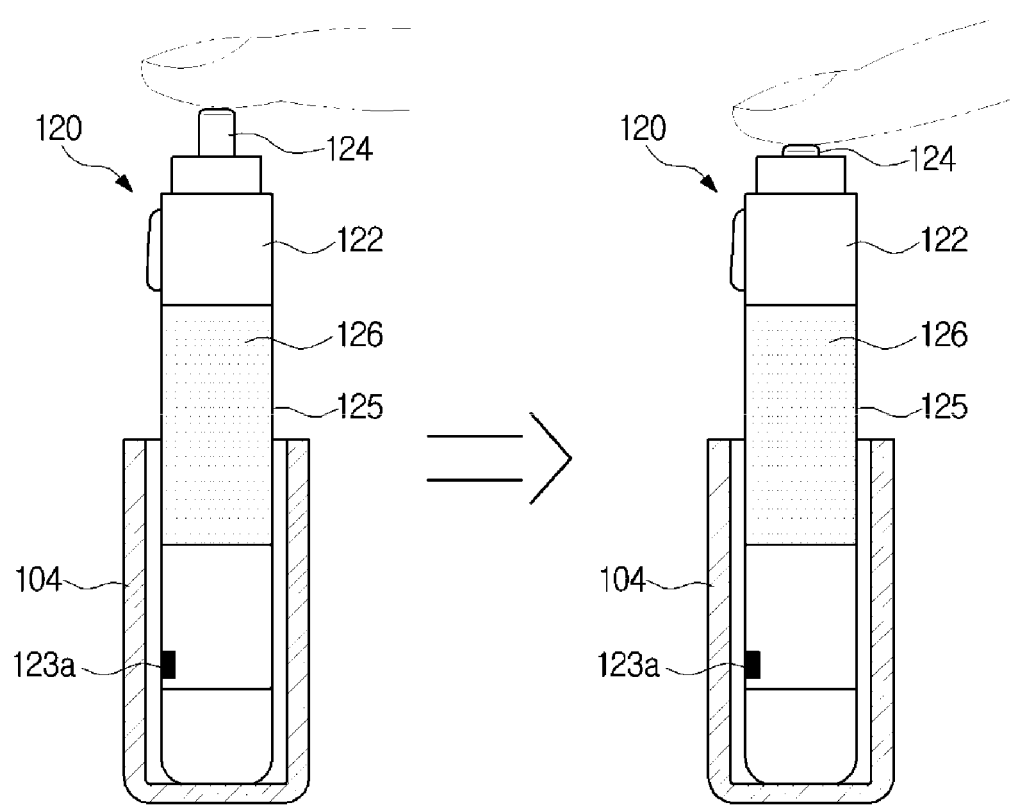
FIG. 11 illustrates a view for describing another example in which an X-ray input apparatus according to an embodiment receives a calibration control command.

FIG. 11 illustrates a view for describing another example in which an X-ray input apparatus according to an embodiment receives a calibration control command.

Referring to the example of FIG. 11, an operator may press the radiation button 124 to input a calibration control command, when the X-ray input apparatus 120 is accommodated in the holder 104.

More specifically, if the operator presses the radiation button 124 without contacting the touch sensor 126 to set a ready state when the X-ray input apparatus 120 is accommodated in the holder 104, it may be determined that a calibration control command is input, and calibration control may be performed.

When pressure that is higher than or equal to the first threshold pressure and lower than the second threshold pressure is applied on the radiation button 124 so that a first command is input, the radiation button 124 may transfer a first signal to the input controller 121. The first signal may be a signal representing that the radiation button 124 has been pressed to set a ready state, or a signal representing that pressure between the first threshold pressure and the second threshold pressure has been applied.

Also, when pressure that is equal to or higher than the second threshold pressure is applied on the radiation button 124 so that a second command is input, the radiation button 124 may transfer a second signal to the input controller 121. The second signal may be a signal representing that the radiation button 124 has been pressed to set a radiation state, or a signal representing that pressure between the second threshold pressure and third threshold pressure has been applied.

When an output of the position sensor 123a represents that the X-ray input apparatus 120 is accommodated in the holder 104, and a first signal has been input from the radiation button 124, the input controller 121 may determine that a calibration control command has been input.

Additionally, the input controller 121 may further determine whether an output of the touch sensor 126 exceeds the capacitance threshold value, that is, whether no touch input is received by the touch sensor 126. When the touch sensor 126 receives no touch input, the input controller 121 may determine that a calibration control command has been input.

If pressing the radiation button 124 of the X-ray input apparatus 120, accommodated in the holder 104, is a calibration control command is input, like the current example, a user's intention can be more definitely reflected, thereby reducing unnecessary calibration.

If the input controller 121 determines that the calibration control command is input, the input controller 121 may perform calibration control according to the above-described operation.

Also, when an output value of the touch sensor 126 is equal to or smaller than the capacitance threshold value, the input controller 121 may determine that an X-ray radiation preparation command or an X-ray radiation command is input, based on a signal output from the radiation button 124.

More specifically, when an output value of the touch sensor 126 is equal to or smaller than the capacitance threshold value, the input controller 121 may determine that an X-ray radiation preparation command is input if the first signal is output from the radiation button 124, and that an X-ray radiation command is input if the second signal is output from the radiation button 124.

Additionally, the input controller 121 may use an output from the position sensor 123a. The input controller 121 may determine that an X-ray radiation preparation command or an X-ray radiation command is input, when an output of the position sensor 123a represents that the X-ray input apparatus 120 has not been accommodated in the holder 104.

When an X-ray radiation preparation command is input, the input controller 121 may transmit an X-ray radiation preparation signal to the holder 104 through the input communication device 127, and when an X-ray radiation command is input, the input controller 121 may transmit an X-ray radiation signal to the holder 104 through the input communication device 127.

Figure 12:
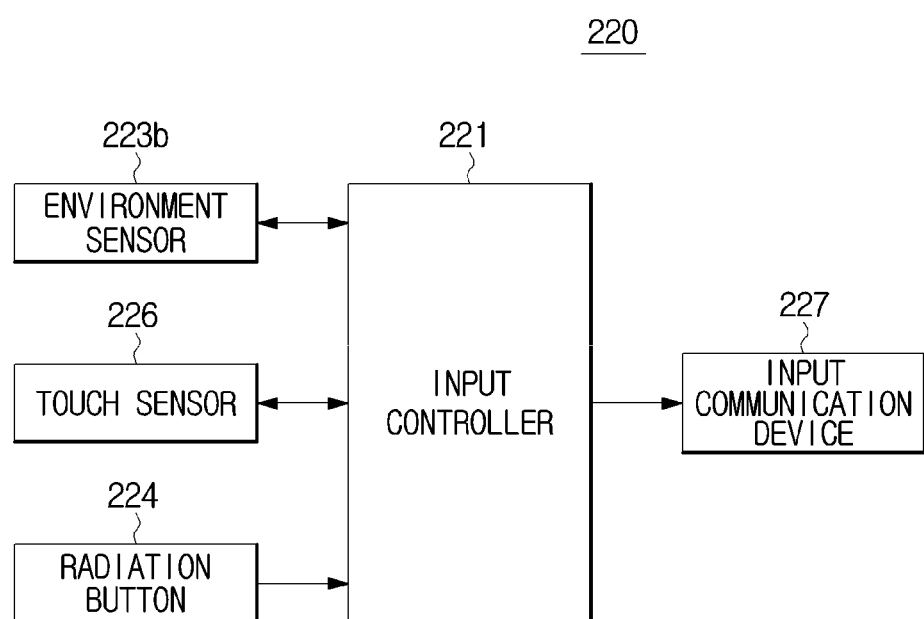
FIG. 12 illustrates a control block diagram of an X-ray input apparatus according to another embodiment.
Figure 13:
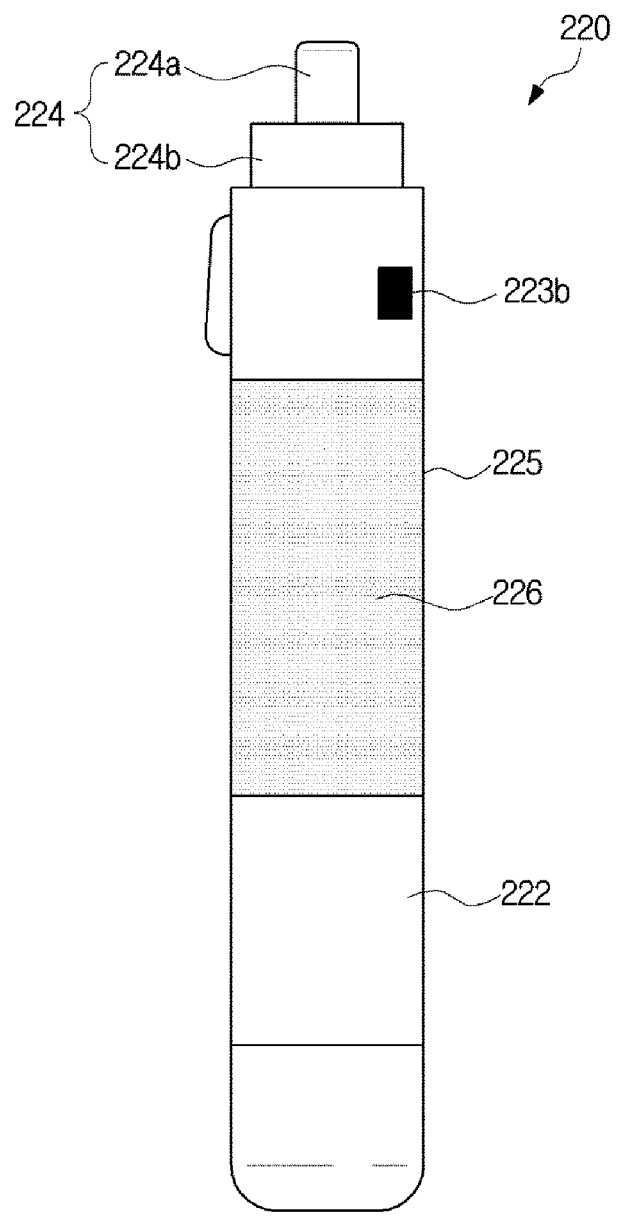
FIG. 13 illustrates an outer appearance of the X-ray input apparatus shown in FIG. 12.
Figure 14:
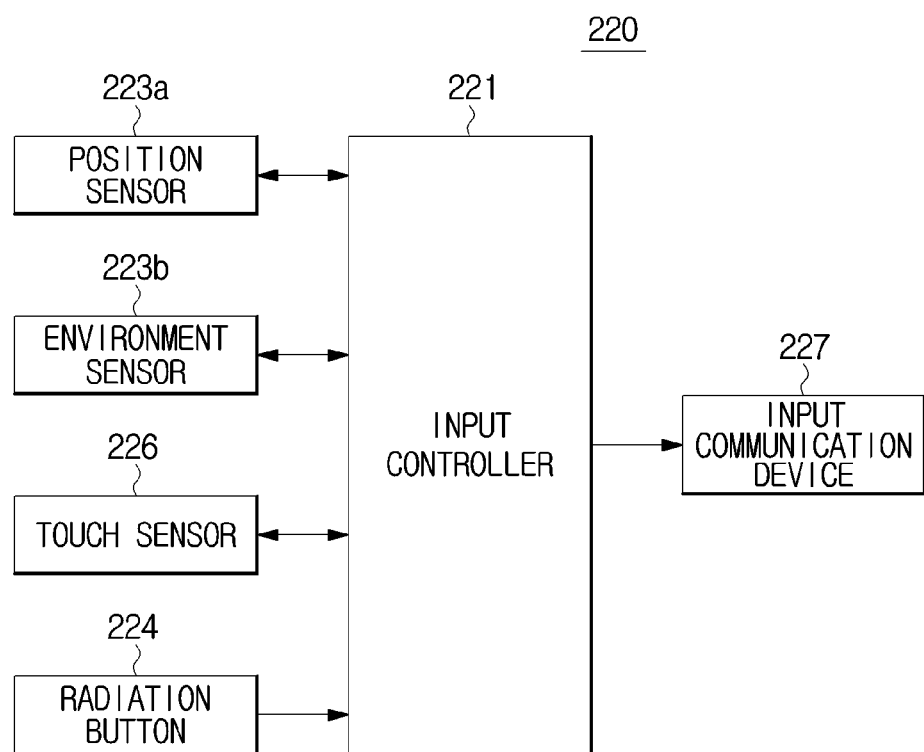
FIG. 14 illustrates a control block diagram of an X-ray input apparatus further including a position sensor.

FIG. 12 illustrates a control block diagram of an X-ray input apparatus according to another embodiment, FIG. 13 illustrates an outer appearance of the X-ray input apparatus shown in FIG. 12, and FIG. 14 illustrates a control block diagram of an X-ray input apparatus further including a position sensor.

Referring to FIGS. 12 and 13, an X-ray input apparatus 220 according to another embodiment may include an environment sensor 223b for acquiring surrounding environment information, a touch sensor 226, a radiation button 224, an input controller 221, and an input communication device 227. The environment sensor 223b may be disposed at an area of a body 222 of the X-ray input apparatus 220.

The input controller 221 may perform calibration control automatically when surrounding environment information acquired by the environment sensor 223b satisfies a calibration condition. The calibration control has been described above in the embodiment of the X-ray input apparatus 120.

The environment sensor 223b may include at least one of a temperature sensor and a humidity sensor. Accordingly, the surrounding environment information acquired by the environment sensor 223b may include temperature information or humidity information.

The environment sensor 223b may sense surrounding environment information in real time or at predetermined time intervals, and transfer the sensed surrounding environment information to the input controller 221.

The input controller 221 may determine whether to perform calibration control, based on an output of the environment sensor 223b. More specifically, the input controller 121 may perform calibration control when the surrounding environment information received from the environment sensor 223b satisfies the calibration condition.

For example, when the temperature information or the humidity information included in the surrounding environment information is out of a reference range, the controller 121 may determine that the calibration condition is satisfied. The reference range may be set to a range of given values, or the reference range may be reset whenever calibration is performed.

When the temperature information or the humidity information is in a reference range, a use environment of the X-ray input apparatus 220 may be assumed to be an environment in which constant temperature and constant humidity are maintained. When a situation in which the environment cannot be maintained occurs, calibration control may be performed to reset a capacitance threshold value. Also, surrounding environment information may be collected periodically even after calibration control is performed, and if the collected temperature or humidity is included out of the reference range, calibration control may be again performed to reset the changed capacitance threshold value.

When the temperature information or the humidity information are out of a reference range, whenever the input controller 121 performs calibration control, temperature or humidity information when the calibration control is performed may be stored, and a reference range may be reset based on the stored temperature or humidity information. If surrounding environment information measured after calibration control is performed is different by a reference value or more from the stored surrounding environment information, it may be determined that the calibration condition is satisfied. In this case, calibration control may be again performed to reset the capacitance threshold value. Temperature or humidity information measured when the calibration control is again performed may also be stored.

According to the current embodiment, by performing calibration control only when calibration control is needed due to a change in surrounding environment, any unnecessary operation can be prevented.

Except for the operation of determining whether to perform calibration control based on an output of the environment sensor 223b, the operation of the touch sensor 226 disposed on the grip area 225 to sense an operator's touch, the operation of the radiation button 224 disposed on the top of the body 222 to receive a ready command and a radiation command, and the related operation of the input controller 221 may be the same as the corresponding operations of the X-ray input apparatus 120 according to the above-described embodiment, and accordingly, detailed descriptions thereof will be omitted.

Meanwhile, as shown in FIG. 14, the X-ray input apparatus 220 according to the other embodiment may further include a position sensor 223a for sensing whether the X-ray input apparatus 220 is accommodated in the holder 104.

Like the position sensor 123a according to the above-described embodiment, the position sensor 223a may include at least one of a magnetic field sensor, a limit switch, an optical sensor, and an ultrasonic sensor. Also, the above descriptions about the position sensor 123a can be applied to the position sensor 223a according to the current embodiment.

The input controller 221 may determine whether the X-ray input apparatus 220 is accommodated in the holder 104, based on an output of the position sensor 223a. If the input controller 221 determines that the X-ray input apparatus 220 is accommodated in the holder 104, the input controller 221 may determine whether to perform calibration control based on surrounding environment information received from the environment sensor 223b. That is, the input controller 221 may perform calibration control when the X-ray input apparatus 120 has been accommodated in the holder 104 and the surrounding environment information is out of a reference range.

Also, whether the surrounding environment information is out of the reference range may be first determined, or whether the surrounding environment information is out of the reference range and whether the X-ray input apparatus 120 has been accommodated in the holder 104 may be simultaneously determined. In other words, whether the X-ray input apparatus 120 has been accommodated in the holder 104 and whether the surrounding environment information is out of the reference range may be determined, and the order of the determinations is not limited.

Also, by including a condition in which no operator contacts the X-ray input apparatus 220 in calibration control conditions, the accuracy of calibration control can be improved. The input controller 121 may perform calibration control, when an output of the environment sensor 223b is out of a reference range, and an output of the touch sensor 226 exceeds a capacitance threshold value.

The operation in which the input controller 121 determines whether to perform calibration control based on surrounding environment information has been described above with reference to FIGS. 12 and 13.

According to the current embodiment, by including a condition in which the X-ray input apparatus 220 has been accommodated in the holder 104 and a condition in which a change in environment occurs in the calibration control conditions, calibration control may be performed as necessary, and when an operator uses the X-ray input apparatus 220, no calibration control may be performed, thereby improving the accuracy of calibration control.

Figure 15:
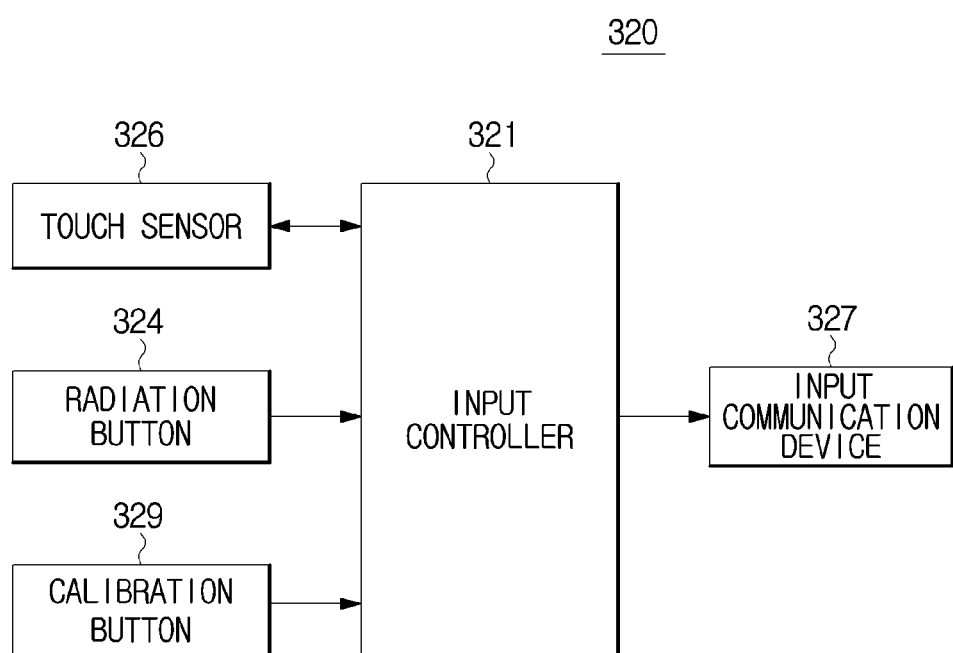
FIG. 15 illustrates a control block diagram of an X-ray input apparatus according to still another embodiment.
Figure 16:
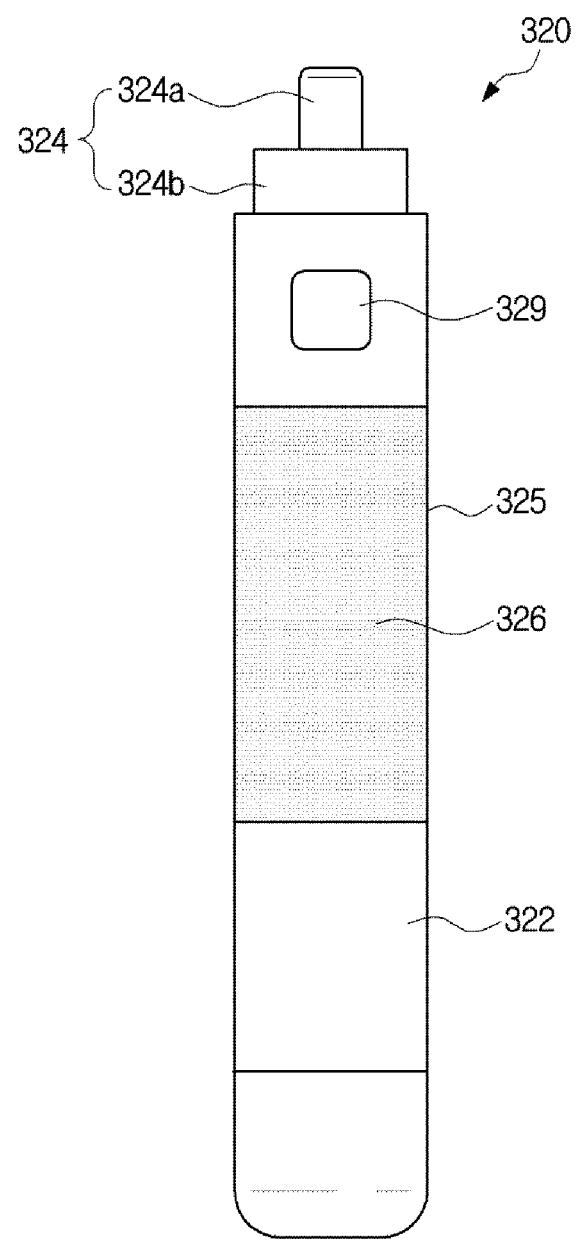
FIG. 16 illustrates an outer appearance of the X-ray input apparatus of FIG. 15.
Figure 17:
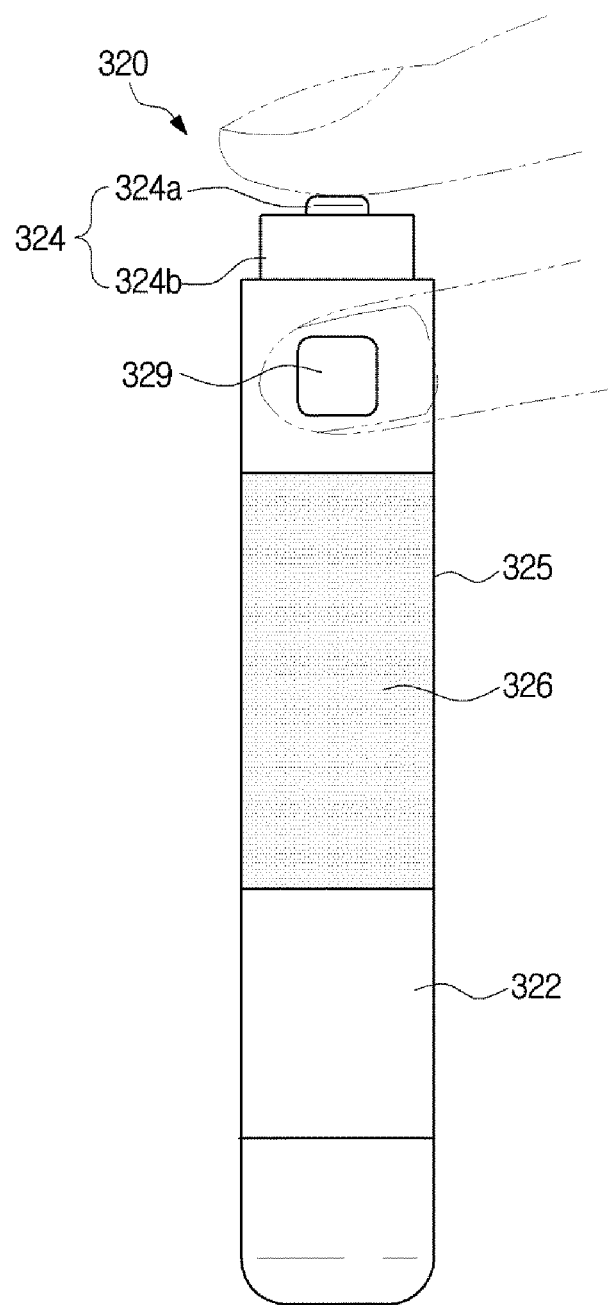
FIG. 17 illustrates a view for describing an operation in which the X-ray input apparatus according to the still another embodiment receives a calibration control command.

FIG. 15 illustrates a control block diagram of an X-ray input apparatus according to still another embodiment, FIG. 16 illustrates an outer appearance of the X-ray input apparatus of FIG. 15, and FIG. 17 illustrates a view for describing an operation in which the X-ray input apparatus according to the still another embodiment receives a calibration control command.

Referring to FIGS. 15 and 16, an X-ray input apparatus 320 according to still another embodiment may include a touch sensor 326, a radiation button 324, an input controller 321, an input communication device 327, and a calibration button 329 provided on an upper area of an outer circumferential surface of a body 322.

The calibration button 329 may be implemented as a button protruding from a surface of the body 322, or as a touch switch.

As shown in FIG. 17, an operator may input a calibration command by pressing the calibration button 329 and the radiation button 324 simultaneously.

If a contact is made on the calibration button 329 or if the calibration button 329 is pressed, the calibration button 329 may generate a third signal, and transfer the third signal to the input controller 321. The third signal may be a signal representing that an operator's input is received, that is, a signal representing that a contact is made on the calibration button 329 or that the calibration button 329 is pressed.

If the input controller 321 receives the third signal from the calibration button 329, and receives a first signal from the radiation button 324, the input controller 321 may determine that a calibration command is input, and perform calibration control. That is, according to the current embodiment, the input controller 321 may determine that a calibration command is input, when the radiation button 324 and the calibration button 329 are pressed simultaneously or when a contact is made simultaneously on the radiation button 324 and the calibration button 329.

By performing calibration control when a signal is input through a combination of the radiation button 324 and the calibration button 329, unintended calibration can be prevented. However, the function of the calibration button 329 is not limited to this, and the calibration button 329 may provide additional functions according to a designer's intention.

Hereinafter, operations of the X-ray imaging apparatus 100 including the X-ray input apparatus 120, 220, or 320 described above will be described in detail.

Figure 18:
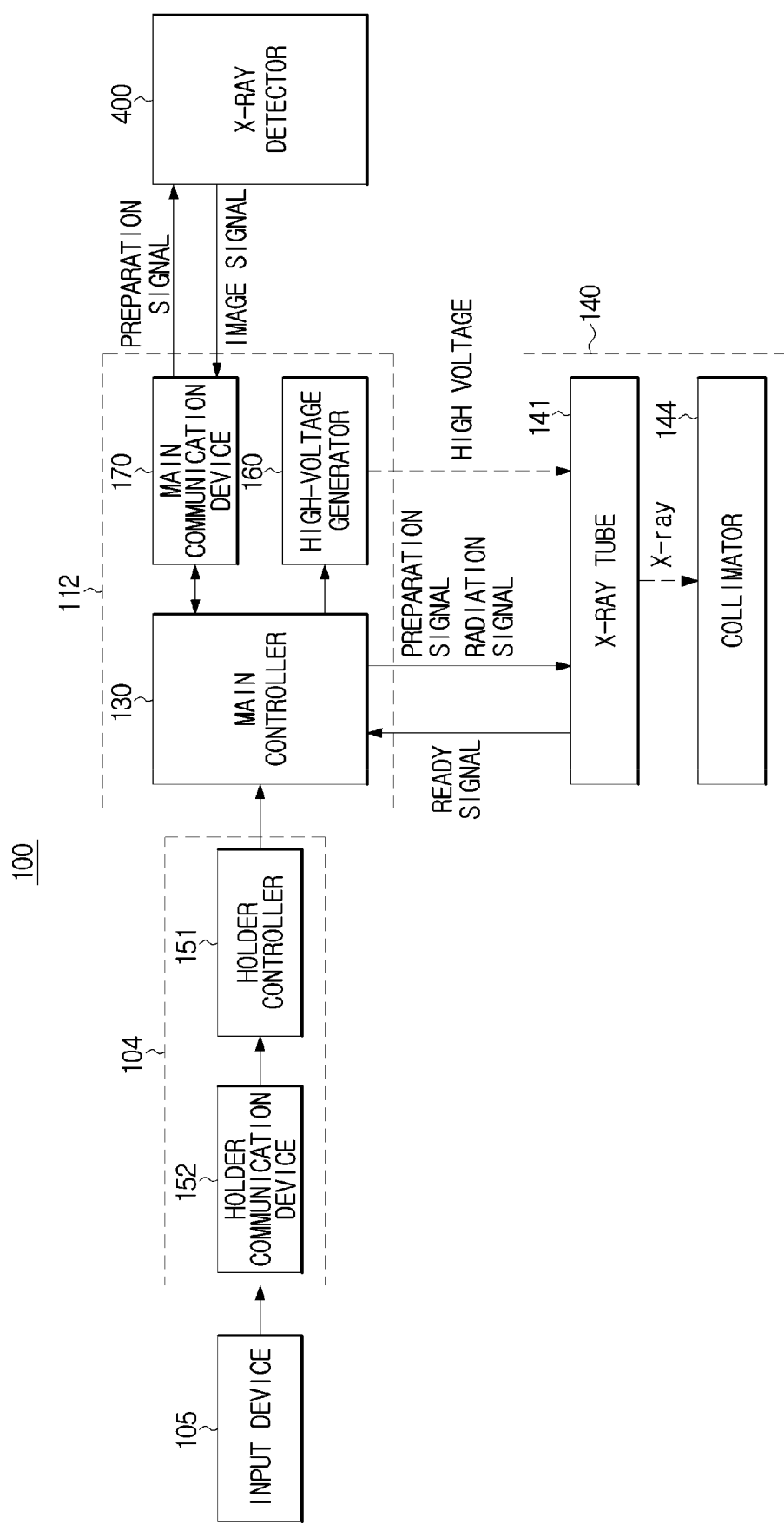
FIG. 18 illustrates a control block diagram of an X-ray imaging apparatus according to an embodiment.

FIG. 18 illustrates a control block diagram of an X-ray imaging apparatus according to an embodiment.

Referring to FIG. 18, the X-ray imaging apparatus 100 may include an input device 105 for receiving a command for controlling the X-ray imaging apparatus 100 from an operator, a holder communication device 152 disposed in the inside of the holder 104 and configured to receive data from the input device 105, a holder controller 151 for converting the data received from the input device 105 to a control signal, a main controller 130 for controlling overall operations of the X-ray imaging apparatus 100, an X-ray source 140 for generating X-rays and irradiating the X-rays, and a high-voltage generator 160 for applying high-voltage energy to the X-ray source 140.

Also, the X-ray source 140 may include an X-ray tube 141 for receiving high-voltage energy generated by the high-voltage generator 160 and for generating X-rays and irradiating the X-rays, and a collimator 144 for guiding a path of the X-rays irradiated by the X-ray tube 141.

An operator may input a command for irradiating X-rays through the input device 105. The input device 105 may include at least one of a switch, a keyboard, a trackball, or a touch screen, or may be provided in the form of a foot switch or a foot pedal.

Also, the input device 105 may be provided in the form of a mobile X-ray input apparatus to which a command can be input when an operator grips the input device 105 with the operator's hand and presses a button with the operator's thumb. The X-ray input apparatus may be provided in the form of a two-step switch. The X-ray input apparatus may be the X-ray input apparatus 120, 220, or 320 according to the above-described embodiment.

As described above, when an output from at least one among the position sensors 123a or 223a, the environment sensor 223b, the calibration button 329, the touch sensor 126, 226, or 326, and the radiation button 124, 224, or 324 represents an input of a calibration control command or satisfies a calibration condition, the input controller 121, 221, or 321 may perform calibration control based on an output of the touch sensor 126, 226, or 326.

When an output value of the touch sensor 126, 226, or 326 is greater than or equal to a capacitance threshold value T1, the input controller 121, 221, or 321 may determine that an X-ray radiation preparation command or an X-ray radiation command is input, based on a signal output from the radiation button 124, 224, or 324. Hereinafter, an operation that is performed when an X-ray radiation preparation command or an X-ray radiation command is input will be described.

If a first signal or a second signal is received from the radiation button 124, 224, or 324 when an output of the touch sensor 126, 226, or 326 is greater than or equal to the capacitance threshold value T1, the input controller 121, 221, or 321 may transmit an X-ray radiation preparation command or an X-ray radiation signal to the holder communication device 152 through the input communication device 127, 227, or 327.

The input communication device 127, 227, or 327 may transfer a signal generated by the X-ray input apparatus 120, 220, or 320 to the holder 104 through a wireless communication method. The input communication device 127 may include at least one of a Wireless Local Area Network (WLAN) module and a short-range communication module. In the present disclosure, the input communication device 127, 227, or 327 may be a WLAN module or a short-range communication module. However, when the X-ray input apparatus 120, 220, or 320 is connected to the holder 104 in a wired fashion, the input communication device 127, 227, or 327 may use wired Ethernet.

The WLAN module may support IEEE1002.11x of the Institute of Electrical and Electronics Engineers (IEEE).

The short-range communication module may be a communication module that supports at least one of various wireless communication methods, such as Bluetooth, Bluetooth low energy, Zigbee communication, Infrared Data Association (IrDA), Wireless-Fidelity (Wi-Fi), Wi-Fi Direct, Ultra Wideband (UWB), Near Field Communication (NFC), and the like. However, the input communication device 127, 227, or 327 is not limited to the above-mentioned examples, and other communication methods well-known to those skilled in the art may be used.

The holder controller 151 may transfer the X-ray radiation preparation signal or the X-ray radiation signal to the main controller 130.

FIG. 18 illustrates and example in which the X-ray input apparatus 120, 220, or 320 transfers an X-ray radiation preparation signal or an X-ray radiation signal to the holder controller 151. However, according to some embodiments, the input controller 121, 221, or 321 may transfer the X-ray radiation preparation signal or the X-ray radiation signal directly to the main controller 130.

The main controller 130 may include at least one memory to store programs for performing the above-described operations and operations which will be described later, and at least one processor to execute the stored programs. Also, the processor included in the main controller 130 may be divided according to operations to be executed. For example, the processor may include a processor for controlling components for X-ray radiation, and a processor for processing image signals transferred from the X-ray detector 400. When the main controller 130 includes a plurality of processors and a plurality of memories, the processors and the memories may be integrated into a single chip, or may be physically divided.

If the main controller 130 receives an X-ray radiation preparation signal from the holder controller 51, the main controller 130 may input an X-ray radiation preparation signal to the high-voltage generator 160.

If the high-voltage generator 160 receives the X-ray radiation preparation signal, the high-voltage generator 160 may start preheating, and if preheating is completed, the high-voltage generator 160 may output a ready signal to the main controller 130.

If the main controller 130 receives the ready signal from the high-voltage generator 160, and receives an X-ray radiation signal from the holder controller 151, the main controller 130 may input an X-ray radiation signal to the high-voltage generator 160. If the high-voltage generator 160 receives the X-ray radiation signal from the main controller 130, the high-voltage generator 160 may generate a high voltage, and apply the high voltage to the X-ray tube 141. The X-ray tube 141 may generate X-rays, and radiate the X-rays. The X-rays radiated from the X-ray tube 141 and then passed through the collimator 144 may be radiated to an object.

The X-rays radiated from the X-ray tube 141 and then passed through the collimator 144 may penetrate the object, and then be radiated to the X-ray detector 400. The X-ray detector 200 may detect the radiated X-rays, and convert the detected X-rays to an electrical signal. The electrical signal converted from the X-rays passed through the object may become an X-ray image signal of the object.

The X-ray detector 400 may be a portable type X-ray detector that can be carried by a user and that can be connected to the X-ray imaging apparatus 100 through wireless communication. The X-ray detector 400 may be included in the X-ray imaging apparatus 100 as a component of the X-ray imaging apparatus 100, or the X-ray detector 400 may be manufactured and sold separately from the X-ray imaging apparatus 100.

The X-ray imaging apparatus 100 may further include a main communication device 170 for communicating with the X-ray detector 400. The main communication device 170 may be a communication module that supports at least one of various wireless communication methods, such as WLAN, Wi-Fi, Bluetooth, Zigbee, Wi-Fi Direct, UWB, IrDA, BLE, NFC, and the like.

The X-ray detector 400 may transmit the X-ray image signal of the object to the main communication device 170, and the main communication device 170 may transfer the X-ray image signal to the main controller 130.

Meanwhile, if the main controller 130 receives an X-ray radiation preparation signal from the holder controller 151, the main controller 130 may transmit the X-ray radiation preparation signal to the X-ray detector 400, as well as the high-voltage generator 160, through the main communication device 170. If the X-ray detector 400 receives the X-ray radiation preparation signal, the X-ray detector 400 may prepare to detect X-rays. When the X-ray detector 400 is ready to detect X-rays, the X-ray detector 400 may transmit a ready signal to the main communication device 170. However, the operation of transmitting the ready signal to the main communication device 170 may be omitted.

If the main controller 130 receives the ready signal from the high-voltage generator 160 and the X-ray detector 400, and receives the X-ray radiation signal from the holder controller 151, the main controller 130 may transfer the X-ray radiation signal to the high-voltage generator 160. As described above, if the high-voltage generator 160 receives the X-ray radiation signal, the high-voltage generator 160 may apply a high voltage to the X-ray source 140 to generate X-rays.

Figure 19:
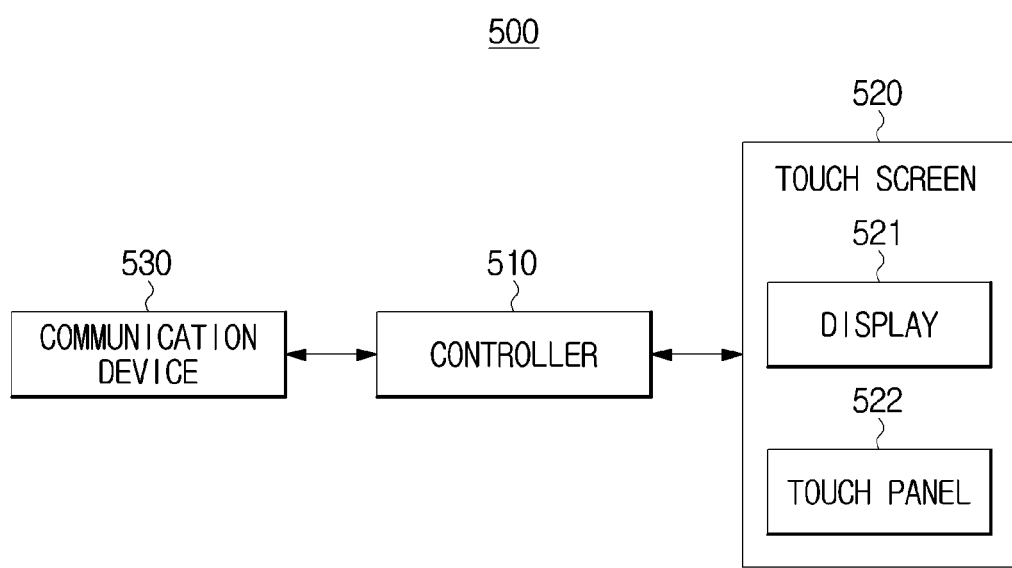
FIG. 19 illustrates a control block diagram of a mobile device that can perform functions of the X-ray input apparatus according to the embodiment.
Figure 20:
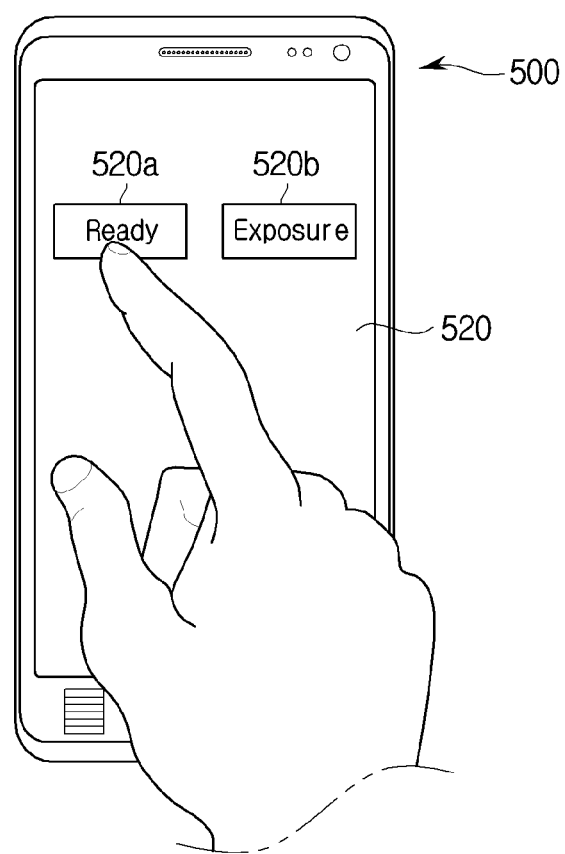
FIGS. 20 and 21 illustrate examples of screens that can be displayed on the mobile device.
Figure 21:
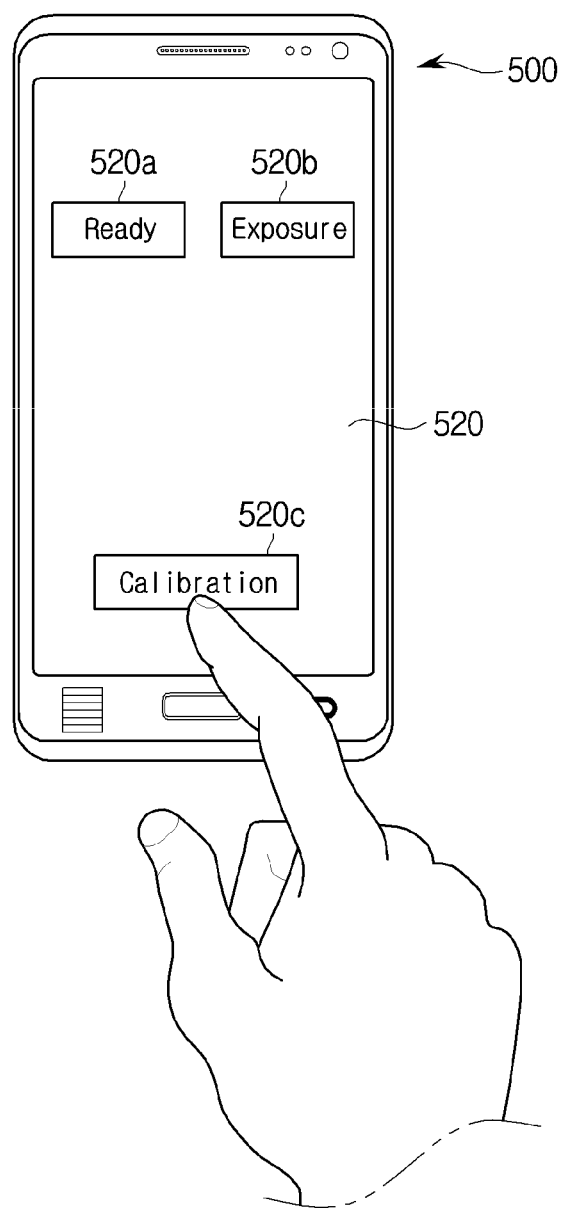

FIG. 19 illustrates a control block diagram of a mobile device that can perform functions of the X-ray input apparatus according to the embodiment, and FIGS. 20 and 21 show examples of screens that can be displayed on the mobile device.

All or some of operations that are performed by the X-ray input apparatus 120, 220, or 320 according to the above-described embodiment may be performed by a mobile device, such as a smart phone, a tablet PC, and Personal Digital Assistant (PDA), including a touch screen.

Referring to FIG. 19, a mobile device 500 may include a touch screen 520, a controller 510, and a communication device 530, and the touch screen 520 may include a display 521, and a touch panel 522 disposed on a front surface of the display 521.

The touch screen 520 may perform a function of a display apparatus to provide a user with visual information, and a function of an input apparatus to receive commands from a user. The function of the display apparatus may be performed by the display 521, and the function of the input apparatus may be performed by the touch panel 522.

The controller 510 may include at least one memory to store programs for performing operations which will be described later, and at least one processor to execute the stored programs.

The controller 510 may control overall operations of the mobile device 500. Accordingly, operations that are performed by the communication device 530 and the touch screen 520 may be controlled by the controller 510, unless otherwise noted.

Operations that are identical to, similar to, or related to operations of the X-ray input apparatus 120, 220, or 320, among operations that are performed by the controller 510, may be performed by executing a related program or a related application installed on the mobile device 500. In the following embodiment, the related program or the related application is called an X-ray radiation control program.

The X-ray radiation control program may control the touch screen of the mobile device 500 to display an X-ray radiation preparation button for receiving an X-ray radiation preparation command and an an X-ray radiation button for receiving an X-ray radiation command. The X-ray radiation control program may execute an X-ray radiation control method for transmitting an X-ray radiation preparation signal to the X-ray imaging apparatus 100 if a touch made on an area corresponding to the X-ray radiation preparation button is sensed, transmitting an X-ray radiation signal to the X-ray imaging apparatus 100 if a touch made on an area corresponding to the X-ray radiation button is sensed, and transmitting neither an X-ray radiation preparation signal nor an X-ray radiation signal if a touch made on the remaining area except for the areas corresponding to the X-ray radiation preparation button and the X-ray radiation button is sensed.

The X-ray radiation control program may be an embedded application installed by default on the mobile device 500, or a third party application received from external recording medium.

When the mobile device 500 receives the X-ray radiation control program from external recording medium, the mobile device 500 may download the X-ray radiation control program from an external server including computer-readable recording medium, and install the X-ray radiation control program to store the X-ray radiation control program in the memory included in the controller 510, wherein a processor included in the controller 510 may execute the stored program to perform the X-ray radiation control method. An embodiment of the X-ray radiation control method that is executed by the mobile device 500 will be described in more detail, later.

The communication device 530 may be a wireless communication module that can perform wireless communication with an external device. For example, the wireless communication module may be at least one of a WLAN module and a short-range communication module. The short-range communication module may be a communication module that supports at least one of various wireless communication methods, such as Bluetooth, Bluetooth low energy, Zigbee communication, IrDA, Wi-Fi, Wi-Fi Direct, UWB, NFC, and the like.

When the mobile device 500 executes the X-ray radiation control program, the controller 510 may control the touch screen 520 to display a ready button 520a for receiving an X-ray radiation preparation command and a radiation button 520b for receiving an X-ray radiation command, as shown in the example of FIG. 20.

A user may touch the ready button 520a or the radiation button 520b to input an X-ray radiation preparation command or an X-ray radiation command.

An output of the touch panel 522 may be transferred to the controller 510, and the controller 510 may determine whether an X-ray radiation preparation command or an X-ray radiation command is input, based on the output of the touch panel 522. Like the above-described embodiment of the X-ray input apparatus 120, 220, or 320, the controller 510 may determine that a touch input is received by the touch panel 522, when the output of the touch panel 522 is smaller than or equal to a predetermined reference value, for example, a capacitance threshold value.

When the touch panel 522 senses a touch made on an area corresponding to the ready button 520a, that is, when an X-ray radiation preparation command is input, the controller 510 may control the communication device 530 to transmit the X-ray radiation preparation signal to the X-ray imaging apparatus 100. For example, if the communication device 530 includes a Bluetooth communication module, the controller 510 may convert the X-ray radiation preparation signal to a Bluetooth packet, and transmit the Bluetooth packet to the X-ray imaging apparatus 100.

Also, when the touch panel 522 senses a touch made on an area corresponding to the radiation button 520b, that is, when an X-ray radiation command is input, the controller 510 may control the communication device 530 to transmit the X-ray radiation command to the X-ray imaging apparatus 100.

Meanwhile, if the touch panel 522 senses a touch made on the remaining area except for the areas corresponding to the ready button 520a and the radiation button 520b, the controller 510 may determine that neither an X-ray radiation preparation command nor an X-ray radiation command are input. In this example, although the ready button 520a or the radiation button 520b is touched, the controller 510 may transmit neither an X-ray radiation preparation signal nor an X-ray radiation signal to the X-ray imaging apparatus 100. Thereby, when the touch screen 520 of the mobile device 500 receives an input made by mistake while a user does not intend to input an X-ray radiation preparation command or an X-ray radiation command, the controller 510 can prevent the high-voltage generator 160 from being preheated unnecessarily, or prevent X-rays from being radiated.

Also, the controller 510 may perform calibration control on the touch panel 522. The calibration control has been described above in the embodiment of the X-ray input apparatus 120, 220, or 320.

The controller 510 may decide time at which calibration control is to be performed, based on an output value of the touch panel 522. For example, the output value of the touch panel 522 may increase or decrease uniformly over the entire area according to a change in temperature. Accordingly, the controller 510 may monitor an output value of the touch panel 522 in real time or periodically, and when a change is generated in the output value of the touch panel 522 in such a way that the output value of the touch panel 522 increases or decreases uniformly over the entire area, the controller 510 may perform calibration control.

Alternatively, as shown in FIG. 21, the touch screen 520 may display a calibration button 520c for receiving a calibration command from a user.

In this example, when the touch panel 522 senses a touch made on an area corresponding to the calibration button 520c, that is, when a calibration command is input, the controller 510 may perform calibration control.

Or, the controller 510 may decide time at which calibration control is to be performed, based on surrounding environment information, like the above-described embodiment of the X-ray input apparatus 220. Hereinafter, the operation will be described with reference to FIG. 22.

Figure 22:
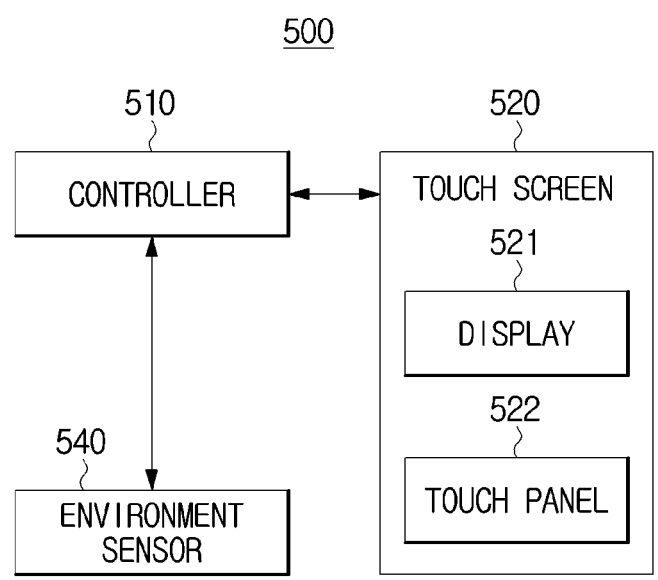
FIG. 22 illustrates a control block diagram of a mobile device that determines a calibration condition based on a change in surrounding environment.

FIG. 22 illustrates a control block diagram of a mobile device that determines a calibration condition based on a change in surrounding environment.

Referring to FIG. 22, the mobile device 500 may further include an environment sensor 540 for acquiring surrounding environment information.

The environment sensor 540 may be at least one of a temperature sensor and a humidity sensor. Accordingly, surrounding environment information acquired by the environment sensor 540 may include temperature information or humidity information.

The environment sensor 540 may sense surrounding environment information in real time or periodically, and transfer the sensed surrounding environment information to the controller 510.

If the controller 510 determines that surrounding environment information received from the environment sensor 223b satisfies the calibration condition, the controller 510 may perform calibration control. For example, if temperature information or humidity information included in the surrounding environment information is out of a predetermined reference range, the controller 510 may determine that the calibration condition is satisfied. The reference range may be set to a range of given values, or the reference range may be reset whenever calibration is performed.

Hereinafter, a method of controlling the X-ray input apparatus 100, according to an aspect, will be described. The above-described embodiments of the X-ray input apparatuses 120, 220, and 320 may be applied to the method of controlling the X-ray input apparatus 100. Accordingly, the descriptions given above with reference to FIGS. 1 to 22 may be applied to the method of controlling the X-ray input apparatus 100 according to an embodiment which will be described below, unless otherwise noted.

Figure 23:
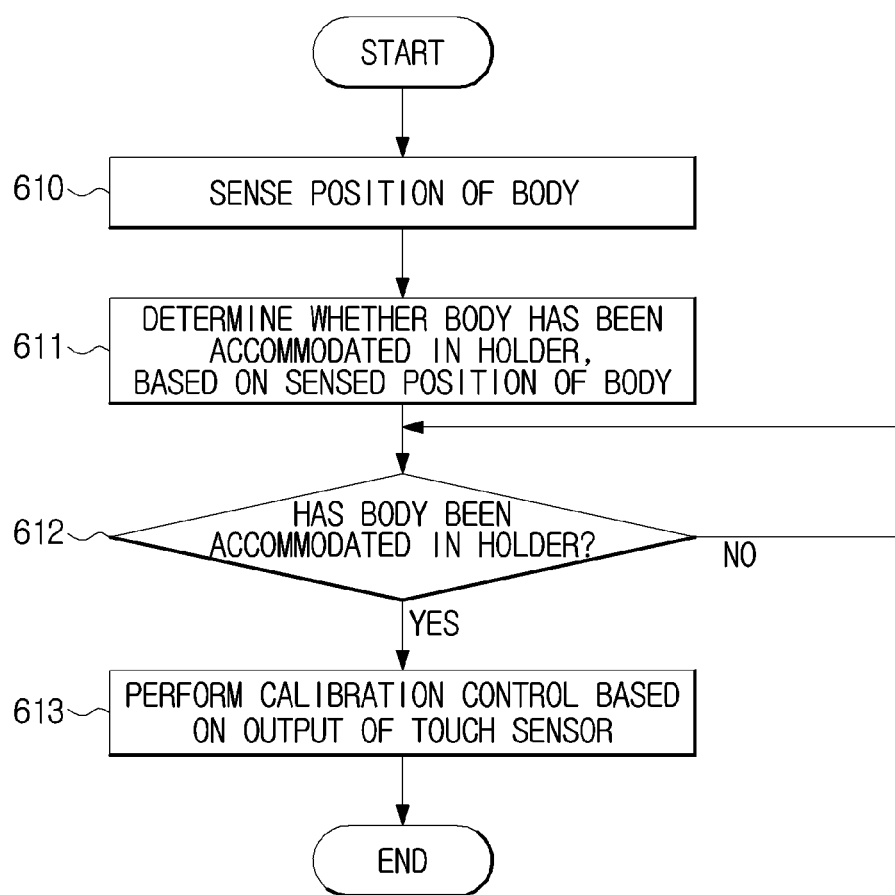
FIGS. 23 and 24 illustrate processes of controlling an X-ray input apparatus according to an embodiment.
Figure 24:
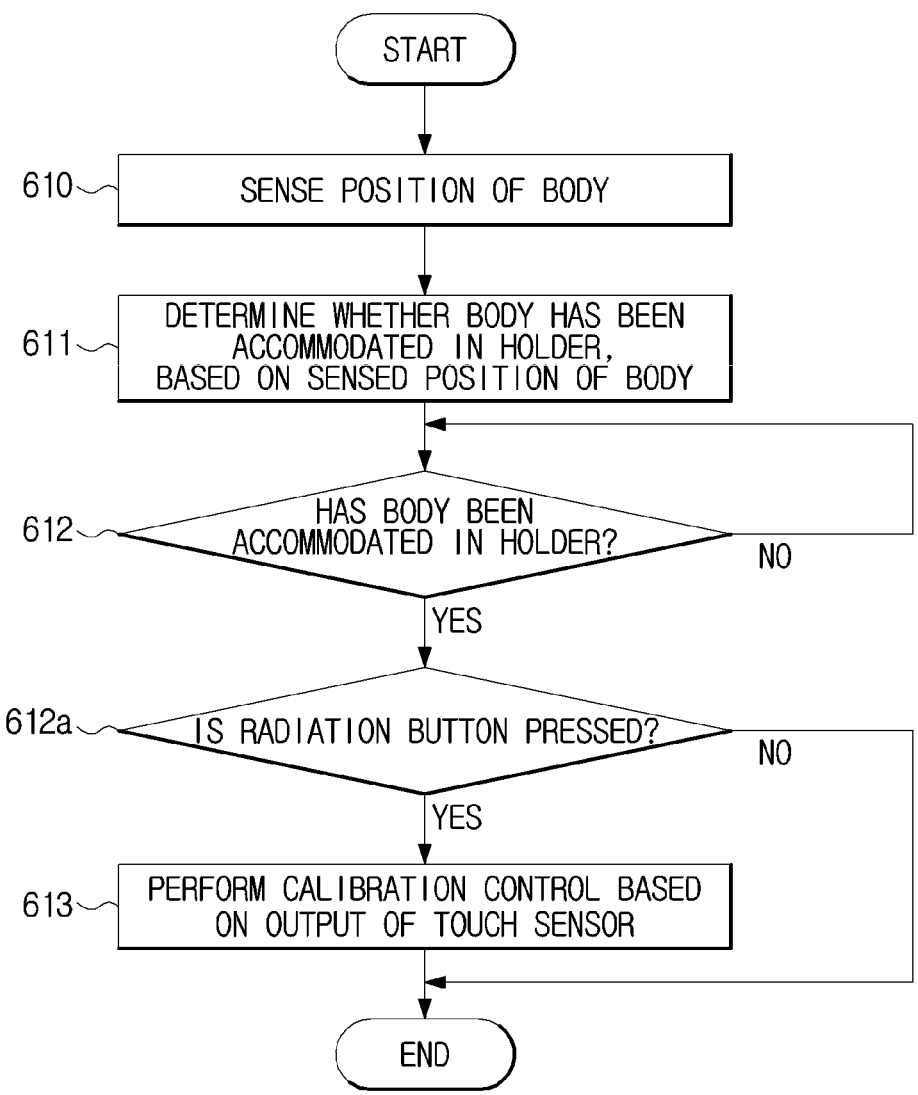

FIGS. 23 and 24 are flowcharts showing a method of controlling an X-ray input apparatus according to an embodiment, and the X-ray input apparatus 120 according to the above-described embodiment may be applied to the method of controlling the X-ray input apparatus 100 according to the current embodiment.

According to the method of controlling the X-ray input apparatus 100, as shown in FIG. 23, a position of the body 122 may be sensed, in operation 610. The position of the body 122 may be sensed by the position sensor 123a disposed at one area of the body 122, and the position sensor 123a may include at least one of a magnetic field sensor, a limit switch, an optical sensor, and an ultrasonic sensor. For example, if the position sensor 123a includes a magnetic field sensor, a magnet may be disposed at an area of the holder 104 corresponding to the position sensor 123a.

Then, it may be determined whether the X-ray input apparatus 100 is accommodated in the holder 104, based on the sensed position of the body 122, in operation 611. A reference value representing that the body 122 is accommodated in the holder 104 may have been stored in advance according to the kind of the position sensor 123a. The reference value may have been stored as a predetermined reference range. The input controller 121 may compare an output from the position sensor 123a to the reference value to determine whether the body 122 is accommodated in the holder 104.

If the input controller 121 determines that the body 122 is accommodated in the holder 104 ("YES" in operation 612), the input controller 121 may receive an output of the touch sensor 126, and perform calibration control based on the output of the touch sensor 126, in operation 613. Referring again to FIG. 10, the received output of the touch sensor 126 may be used as a capacitance reference value C1, and a capacitance threshold value T1 may be decided based on a pre-stored minimum value D of changes in capacitance and the capacitance reference value C1 to thereby perform calibration control.

Meanwhile, the input controller 121 may additionally use an output of the touch sensor 126 to determine whether to perform calibration control. In this example, when the X-ray input apparatus 120 is accommodated in the holder 104 and an output of the touch sensor 126 exceeds the capacitance threshold value T1, the input controller 121 may perform calibration control.

Also, in order to further improve the input accuracy of a calibration control command, as shown in FIG. 24, the input controller 121 may determine whether the radiation button 124 is pressed, in operation 612a. When the input controller 121 determines that the radiation button 124 is pressed ("YES" in operation 612a), the input controller 121 may determine that a calibration control command is input. For example, when pressure that is higher than or equal to first threshold pressure and lower than second threshold pressure is applied on the radiation button 124 so that a first signal is output from the radiation button 124, the input controller 121 may determine that the radiation button 124 is pressed, so that a calibration control command is input.

Figure 25:
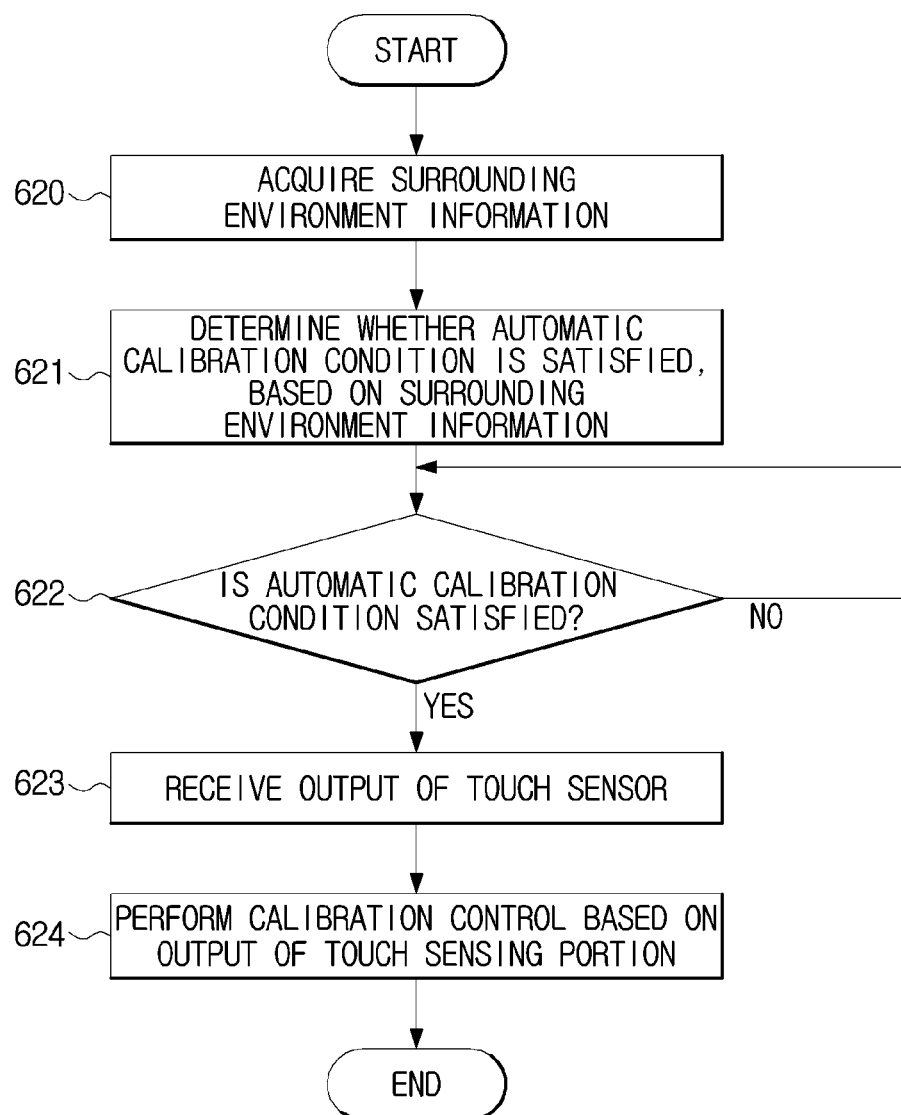
FIGS. 25 and 26 illustrate processes of controlling an X-ray input apparatus, according to another embodiment.
Figure 26:
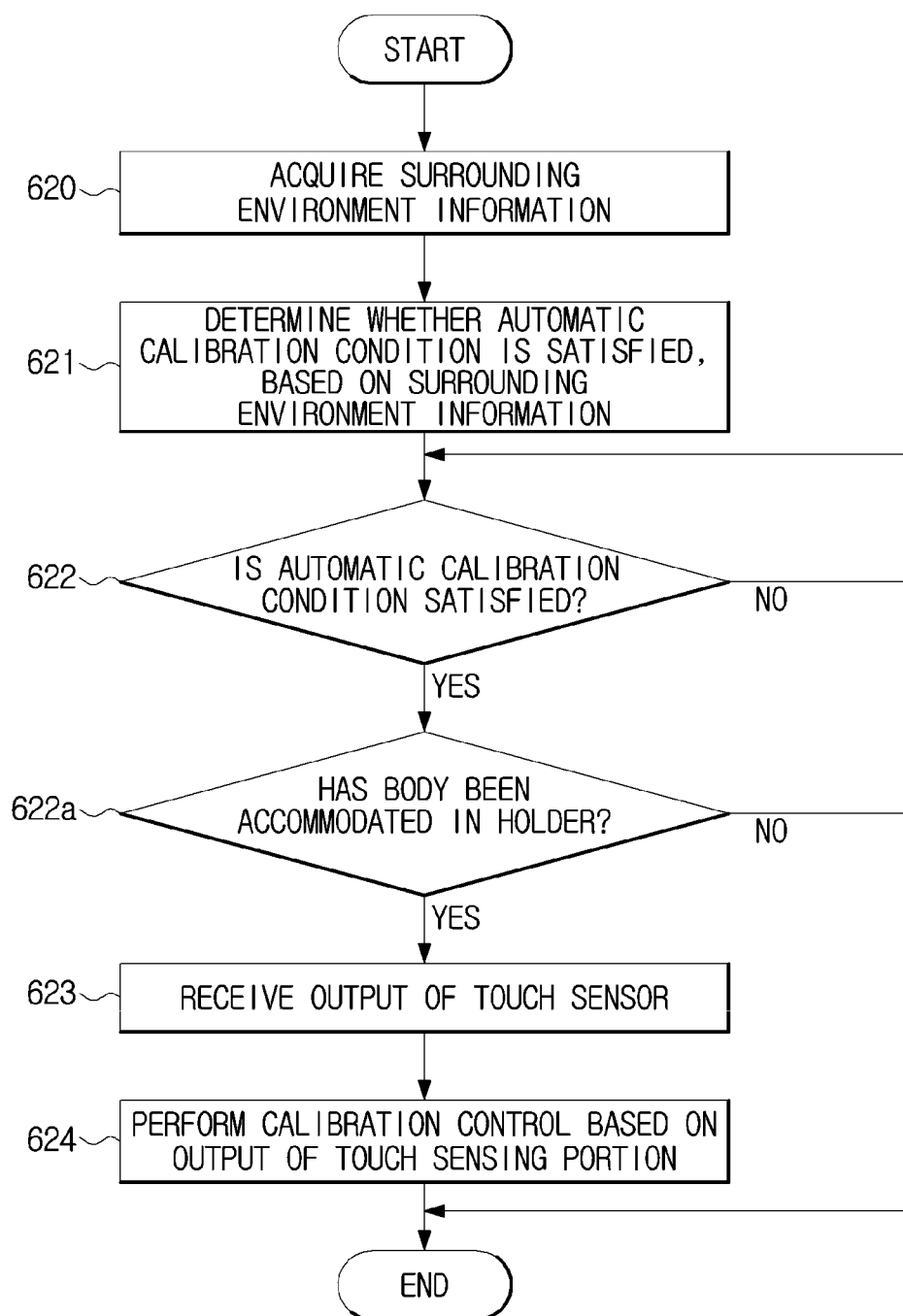

FIGS. 25 and 26 are flowcharts illustrating a method of controlling an X-ray input apparatus, according to another embodiment. The X-ray input apparatus 220 according to the other embodiment as described above may be applied to the method of controlling the X-ray input apparatus, according to the current embodiment.

According to the method of controlling the X-ray input apparatus, as shown in FIG. 25, surrounding environment information may be acquired, in operation 620. The surrounding environment information may be acquired by the environment sensor 223b disposed on one area of the body 222, and the environment sensor 223b may include at least one of a temperature sensor and a humidity sensor. Accordingly, the acquired surrounding environment information may include at least one of temperature information and humidity information.

Then, it may be determined whether an automatic calibration condition is satisfied, based on the surrounding environment information, in operation 621. For example, if the surrounding environment information is out of a reference range, it may be determined that an automatic calibration condition is satisfied, and calibration control may be automatically performed. The reference range may be set to a range of given values, or the reference range may be reset whenever calibration is performed. The reference range for determining an automatic calibration condition has been described above in detail in the embodiment of the X-ray input apparatus 220.

If the automatic calibration condition is satisfied ("YES" in operation 622), an output of the touch sensor 226 may be received, in operation 623, and calibration control may be performed based on the output of the touch sensing portion 126, in operation 624.

Also, a condition in which the X-ray input apparatus 220 is accommodated in the holder 104 may be added in the automatic calibration condition. In this example, as shown in FIG. 26, it may be determined whether the X-ray input apparatus 220 is accommodated in the holder 104, based on the position of the body 222, in operation 622a. If it is determined that the body 222 is accommodated in the holder 104 ("YES" in operation 622a), an output of the touch sensor 226 may be received, and calibration control may be performed based on the output of the touch sensor 226, in operation 624.

According to another example, an operator's non-contact may be added in the automatic calibration condition. In this example, when an output of the environment sensor 223b is out of a reference range and an output of the touch sensor 226 exceeds a capacitance threshold value, the input controller 221 may perform calibration control.

In FIG. 26, whether the surrounding environment information is out of the reference range may be first determined, however, the method of controlling the X-ray input apparatus 220 is not limited to this. In other words, the order of a determination on whether the X-ray input apparatus 220 is accommodated in the holder 104 and a determination on whether surrounding environment information is out of the reference range is not limited.

Figure 27:
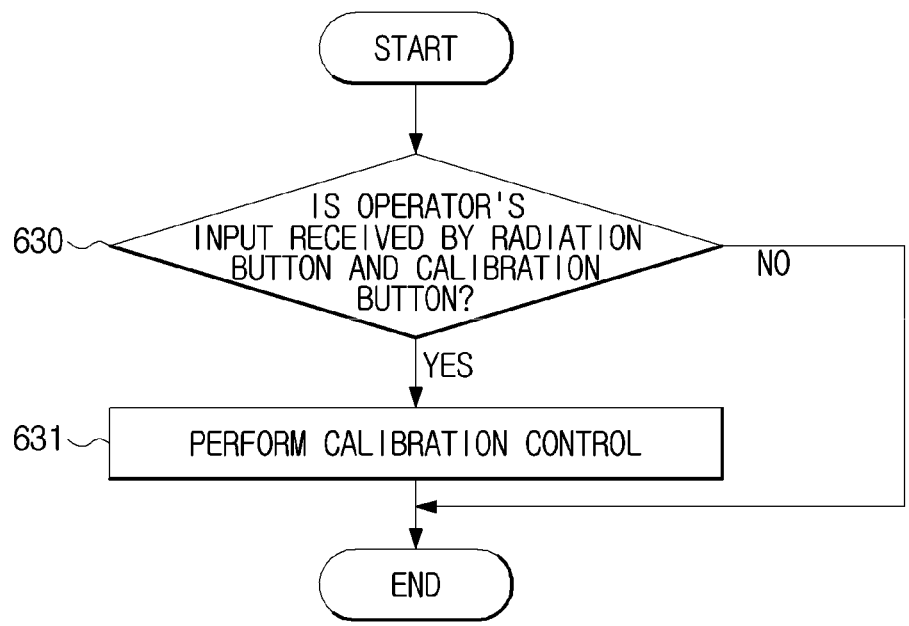
FIG. 27 illustrates a process of controlling an X-ray input apparatus, according to still another embodiment.

FIG. 27 illustrates a process of controlling an X-ray input apparatus, according to still another embodiment. The X-ray input apparatus 320 according to the above-described embodiment may be applied to the method of controlling the X-ray input apparatus, according to the current embodiment.

According to the method of controlling the X-ray input apparatus 320 as shown in FIG. 27, when an operator's input is received by the radiation button 324 and the calibration button 329 ("YES" in operation 630), it may be determined that a calibration control command is input, and calibration control may be performed, in operation 631.

According to the current embodiment, the operator may input a calibration command by pressing the calibration button 329 and the radiation button 324 simultaneously. If a contact is made on the calibration button 329 or if the calibration button 329 is pressed, the calibration button 329 may generate a third signal and transfer the third signal to the input controller 321. If the input controller 321 receives the third signal from the calibration button 329 and receives a first signal from the radiation button 324, the input controller 321 may determine that a calibration command is input.

Additionally, the input controller 321 may additionally use an output of the touch sensor 326 to determine whether to perform calibration control. In this example, when the input controller 321 receives the third signal from the calibration button 329 and receives the first signal from the radiation button 324, the input controller 321 may perform calibration control if the output of the touch sensor 326 exceeds a capacitance threshold value.

In the X-ray input apparatus, the X-ray imaging apparatus including the same, and the method of controlling the X-ray input apparatus according to the above-described embodiments, by performing calibration control only when a user intends to perform calibration control or when calibration control is needed, it is possible to prevent calibration control from being performed unnecessarily and inaccurately.

The X-ray input apparatus and the control method thereof according to the present disclosure can expect the following effects.

First, by performing calibration control only when the X-ray input apparatus is accommodated in the holder, accuracy in operation of the X-ray input apparatus may be improved.

Also, by performing calibration control on the touch sensor when a preparation signal for each of a plurality of input devices is output, accuracy in operation of the X-ray input apparatus may be improved.

Also, by performing calibration control on the touch sensor based on sensor value information of the sensor installed in the X-ray input apparatus, it is possible to perform automatic calibration control on the touch sensor without a user's separate operation.

Although a few embodiments of the present disclosure have been shown and described, it would be appreciated by those skilled in the art that changes may be made in these embodiments without departing from the principles and spirit of the disclosure, the scope of which is defined in the claims and their equivalents.

Although the present disclosure has been described with various embodiments, various changes and modifications may be suggested to one skilled in the art. It is intended that the present disclosure encompass such changes and modifications as fall within the scope of the appended claims.

What is claimed is:

1. An X-ray imaging apparatus comprising:
a holder having communication circuitry; and
an X-ray input apparatus configured to be removably mounted in the holder,
wherein the X-ray input apparatus comprises:
a body;
a communication circuitry disposed in the body and configured to communicate with the communication circuitry in the holder;
a first sensor configured to detect a touch on an outer circumferential surface of the body;
a button configured to receive a user input;
a second sensor configured to detect whether the X-ray input apparatus is mounted in the holder; and
a controller configured to:
determine whether the X-ray input apparatus is mounted in the holder based on a first signal received from the second sensor,
in response to determining that the X-ray input apparatus is mounted in the holder, calibrate a sensitivity of the first sensor,
while the X-ray input apparatus is removed from the holder, determine that the user input is received via the button, and
in response to receiving the user input, control the communication circuitry to transmit a command signal to the communication circuitry in the holder if a signal received from the calibrated first sensor corresponds to a hand-gripping.

2. The X-ray imaging apparatus according to claim 1, wherein the controller is configured to perform the calibration based on the signal received from the first sensor.

3. The X-ray imaging apparatus according to claim 2, wherein the signal received from the first sensor comprises a capacitance value.

4. The X-ray imaging apparatus according to claim 2, wherein the signal received from the first sensor comprises a reference signal corresponding to a signal output by the first sensor.

5. The X-ray imaging apparatus according to claim 4, wherein the controller is configured to receive the reference signal from the first sensor when the body is mounted in the holder, and calibrate the sensitivity of the first sensor by determining a threshold value for detecting the touch based on the reference signal.

6. The X-ray imaging apparatus according to claim 1, wherein the controller is configured to calibrate the sensitivity of the first sensor based on receiving the user input and the determination that the X-ray input apparatus is mounted in the holder.

7. The X-ray imaging apparatus according to claim 1, wherein the button comprises:
a one-step button configured to receive an X-ray radiation preparation command and output a first signal when a predetermined pressure is applied on the one-step button; and
a two-step button configured to receive an X-ray radiation command, and output a second signal when a predetermined pressure is applied on the two-step button.

8. The X-ray imaging apparatus according to claim 7, wherein the controller is configured to calibrate the sensitivity of the first sensor based on a reception of the first signal and the determination that the X-ray input apparatus is mounted in the holder.

9. The X-ray imaging apparatus according to claim 8, further comprising a second button disposed with respect to the body, and configured to output a third signal when a predetermined pressure is applied on the second button.

10. The X-ray imaging apparatus according to claim 9, wherein the controller is configured to calibrate the sensitivity of the first sensor based on the reception of the first signal, a reception of the third signal and the determination that the X-ray input apparatus is mounted in the holder.

11. The X-ray imaging apparatus according to claim 1, further comprising:
an X-ray source configured to irradiate the X-rays;
a high-voltage generator configured to apply a high voltage to the X-ray source; and
a main controller configured to transmit at least one of an X-ray radiation preparation signal or an X-ray radiation signal to the high-voltage generator according to a control command input from the button.

12. An X-ray imaging apparatus comprising:
a holder having communication circuitry; and
an X-ray input apparatus configured to be removably mounted in the holder,
wherein the X-ray input apparatus comprises:
a body;
a communication circuitry disposed in the body and configured to communicate with the X-ray imaging apparatus;
touch sensor configured to detect a touch on an outer circumferential surface of the body;
a button configured to receive a user input; and
a controller configured to:
based on the X-ray input apparatus being mounted in the holder, calibrate a sensitivity of the touch sensor,
after the touch sensor has been calibrated and while the X-ray input apparatus is removed from the holder, determine that the user input is received via the button, and
in response to receiving the user input, control the communication circuitry to transmit a command signal to the X-ray imaging apparatus based on signals received from the touch sensor previously calibrated while the X-ray input apparatus mounted in the holder.

13. The X-ray imaging apparatus to claim 12, wherein controller is configured to calibrate the sensitivity of the touch sensor based on signals received from the touch sensor.

14. The X-ray imaging apparatus according to claim 13, wherein each of the signals received from the touch sensor comprises a capacitance value.

15. The X-ray imaging apparatus according to claim 13, wherein each of the signals received from the touch sensor comprises a reference signal corresponding to respective signals output by each of the touch sensor when no touch is detected by the touch sensor.

16. The X-ray imaging apparatus according to claim 15, wherein the controller is configured to receive the reference signal from the each of the touch sensor when the body is mounted in the holder, and calibrate the sensitivity of the touch sensor by determining a threshold value for detecting the touch based on the reference signal.

17. The X-ray imaging apparatus according to claim 12, further comprising a position sensor, and wherein the controller is further configured to determine whether the X-ray input apparatus is mounted in the holder based on a signal received from the position sensor.

18. An X-ray imaging apparatus comprising:
a holder having communication circuitry; and
an X-ray input apparatus configured to be removably mounted in the holder,
wherein the X-ray input apparatus comprises:
  a body;
  a communication circuitry disposed in the body and configured to communicate with the X-ray imaging apparatus;
  a touch sensor configured to detect a touch on an outer circumferential surface of the body;
  a button configured to receive a user input;
  a position sensor configured to detect whether the X-ray input apparatus is mounted in the holder; and
  a controller configured to:
    determine whether the X-ray input apparatus is mounted in the holder based on a signal received from the position sensor,
    calibrate a sensitivity of the touch sensor when it is determined that the X-ray input apparatus is mounted in the holder, and
    control the communication circuitry to transmit a command signal to the X-ray imaging apparatus in response to receiving the user input through the button and detecting the touch through the touch sensor.

19. The X-ray imaging apparatus according to claim 18, wherein the controller is configured to calibrate the sensitivity of the touch sensor based on a signal received from the touch sensor.

20. The X-ray imaging apparatus according to claim 19, wherein the signal received from the touch sensor is a reference signal corresponding to a signal output by the touch sensor when no touch is detected by the touch sensor.

21. The X-ray imaging apparatus according to claim 1, wherein the controller is further configured to determine that the X-ray input apparatus is removed from the holder based on a second signal received from the second sensor after the first sensor has been calibrated.

* * * * *